US007071177B2

(12) United States Patent
Krauss et al.

(10) Patent No.: US 7,071,177 B2
(45) Date of Patent: Jul. 4, 2006

(54) P-(SULFONYL) ARYL AND HETEROARYLAMINES AS ANTI-INFLAMMATORY AGENTS

(75) Inventors: Nancy Elisabeth Krauss, Sunnyvale, CA (US); Taraneh Mirzadegan, Los Altos, CA (US); David Bernard Smith, San Mateo, CA (US); Keith Adrian Walker, Los Altos Hills, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/844,061

(22) Filed: Apr. 26, 2001

(65) Prior Publication Data
US 2002/0052349 A1 May 2, 2002

Related U.S. Application Data

(60) Provisional application No. 60/200,310, filed on Apr. 28, 2000.

(51) Int. Cl.
*A01N 51/00* (2006.01)
*A61K 31/63* (2006.01)
*C07D 251/00* (2006.01)

(52) U.S. Cl. .............. 514/155; 514/316; 544/180; 544/194; 544/238; 544/92; 544/284; 544/287; 546/152; 546/179; 546/193; 546/201

(58) Field of Classification Search ............... 564/374, 564/384; 514/646, 658, 155, 316; 544/180, 544/194, 238, 92, 284, 287; 546/152, 179, 546/193, 201
See application file for complete search history.

(56) References Cited

U.S. PATENT DOCUMENTS

| | | | | |
|---|---|---|---|---|
| 3,615,606 | A | 10/1971 | Schulte et al. | ................. 96/100 |
| 4,277,492 | A | 7/1981 | Daniel et al. | ................ 424/304 |
| 4,857,530 | A * | 8/1989 | Berman et al. | ............. 514/259 |
| 4,987,023 | A * | 1/1991 | Sato et al. | .................. 428/215 |
| 5,538,976 | A * | 7/1996 | Okada et al. | ................ 514/256 |
| 5,952,349 | A * | 9/1999 | Asberom et al. | ........... 514/316 |

FOREIGN PATENT DOCUMENTS

| | | | |
|---|---|---|---|
| EP | 0 757 037 A2 | 2/1997 | |
| WO | WO 98/01425 | * | 1/1998 |
| WO | WO 98/01425 A | | 1/1998 |
| WO | WO 9801425 A1 | * | 1/1998 |
| WO | WO 98/25893 | | 6/1998 |
| WO | WO 98/50029 | * | 11/1998 |
| WO | WO9850023 | * | 11/1998 ................. 514/256 |
| WO | WO 01/17982 A1 | | 3/2001 |

OTHER PUBLICATIONS

CAS printout for Sebti, Chem. Abs. 130: 25338.*
CAS printout for Hirsch et al, Chem. Abs. 86: 197939.*
CAS printout for Okada et al. 127:242825.*
CAS printout for Barton et al.*
CAS printout for Mattor et al.*
CAS printout for Asberrom et al. Chem. Abs. 131:214192.*
CAS printout for Dinsmore et al. Chem. Abs. 132: 160824.*
CAS printout for Sebti et al. Chem. Abs. 130: 25338.*
CAS printout for Okada et al. Chem. Abs. 127;242825.*
Balinska et al. "Effect of Combined Inhibitors of Thymidylate Synthase ... ", Anticancer Research 17: 4519-4524 (1997).*
Balinska et al. "The effects of combined antifolates on inhibition of growth of murine leukemia cells curtured in vitro", Acta Biochmica Polonica vol. 44, No. Apr. 1997, p. 743-750.*
Okada et al. "Studies on Aromatase Inhibitiors IV ... ", Chem. Pharm. Bull. 45(8) 1293-1299 (1997).*
Jones et al., "Structure based Design of Lipophilic Quinazoline Inhibitors of Thymidylate Synthase", J. Med. Chem. 1996, 39, 904-917.*
Dinsmore et al., "Imidazole-Containing Diarylether and diarylsulfone inhibitors of farnesyl-protein transferase", Bioorganic & Medicinal Chemistry Letters 9 (1999) 3301-3306.*
Barton, et al., "The Invention of Radical Reactions. 30. Diazirines as Carbon Radical Traps. Mechanistic Aspects and Synthetic Applications of a Novel and Efficient Amination Process", *J. American Chemical Soc.*, (1993) pp 8050-8059, vol. 115.

(Continued)

*Primary Examiner*—James O. Wilson
*Assistant Examiner*—Paul V. Ward
(74) *Attorney, Agent, or Firm*—Grant D. Green

(57) ABSTRACT

This invention relates to anti-inflammatory and analgesic compounds, especially to certain p-(sulfonyl)phenyl amino derivatives, pharmaceutical compositions containing them, methods for their use, and methods for preparing these compounds.

25 Claims, No Drawings

OTHER PUBLICATIONS

McNamara, et al., "Potent Inhibition of Thymidylate Synthase by Two Series of Nonclassical Quinazolines", *J. Med. Chem.*, (1990) pp 2045-2051, vol. 33.

Jones, et al., "Structure-Based Design of Lipophilic Quinazoline Inhibitors of Thymidylate Synthase", *J. Med. Chem.*, (1996) pp 904-917, vol. 39.

Chemical Abstracts, No. 86:155606 (1977), p. 469, vol. 86 Djudovic, et al., "Synthesis of quinoline-3- and quinoxaline-2 derivatives and their effect against various malarial causative organisms", Pharmazie (1976), pp 845-849, vol. 31:12.

Chemical Abstracts, No. 84:30945 (1976), p. 452, vol. 84 Kutla, "Condensation products of saccharin with some amines", Istanbul University Eczacilik Fak. Mecm., (1975), pp 5-7, vol. 11:1.

Dinsmore, et al., "Imidazole-Containing Diarylether and Diarysulfone Inhibitors of Farnesyl-Protein Transferase," *Bioorganic & Medicinal Chemistry Letters*, (1999) pp 3301-3306, vol. 9:23.

Desai, et al., "Studies in Sulphanilamide and Allied Compounds," *Indian J. Pharm.*, (1951) pp 211-213, No. 13, XP-000926589.

Billman, et al., "The Reductive Acylation of Schiff Bases Using Trimethylamine Borane," *J. Org. Chem.*, (1962) pp 2640-2643, vol. 27, XP-001015561.

Katritzky, et al., "A Novel Method for the Preparation of 3-Amino-4-Hydroxybenzenefulfonamide Precursors of "Acid Alizarin Violet N" Derivatives," (1993) *Synth. Commun.*, pp 405-417, vol. 23:3 XP-000926588.

* cited by examiner

P-(SULFONYL) ARYL AND HETEROARYLAMINES AS ANTI-INFLAMMATORY AGENTS

CROSS REFERENCE TO RELATED APPLICATIONS

Pursuant to 35 U.S.C. §119(e), this application claims priority to the filing date of the U.S. Provisional Patent Application Ser. No. 60/200,310, filed Apr. 28, 2000 the disclosure of which is herein incorporated by reference.

BACKGROUND OF THE INVENTION

1. Field of the Invention

This invention relates to anti-inflammatory and analgesic compounds, especially to certain p-(sulfonyl)-aryl and -heteroaryl amines, pharmaceutical compositions containing them, methods for their use, and methods for preparing these compounds.

2. Description of the Related Art

U.S. Pat. No. 4,277,492 (Dow Chemical) discloses 4-bis ((phenylmethyl)amino)benzensulfonic acids and their pharmaceutically-acceptable salts useful as antiviral agents.

U.S. Pat. No. 4,857,530 (Warner-Lambert) discloses 6-substituted-4(3H)-quinazolinones which inhibit the enzyme thymidylate synthase and thus are useful as anti-cancer agents.

U.S. Pat. No. 5,538,976 (Yamanouchi Pharmaceutical) discloses substituted tertiary amino compounds, one of the substituents being a pyrimidine ring, a pyridazine ring, or a triazine ring, or pharmaceutically acceptable salts thereof. These compounds have aromatase inhibiting activity and are useful as a prophylactics and/or therapeutic agents for breast cancer, mastopathy, endometriosis, prostatic-hypertrophy, and so forth.

WO 98/25893 (Athena Neurosciences) discloses arylsulfonamides which have activity as inhibitors of phospholipase $A_2$, inhibitors of cytokine release, and as inhibitors of neurodegeneration.

WO 98/50029 (University of Pittsburgh) discloses certain substituted benzenesulfonamides as inhibitors of protein isoprenyl transferases.

EP 757037 A2 (Ono Pharmaceutical) discloses certain benzenesulfonyl amino acids as metalloproteinase inhibitors.

SUMMARY OF THE INVENTION

In a first aspect, this invention provides compounds selected from the group of compounds represented by formula (I):

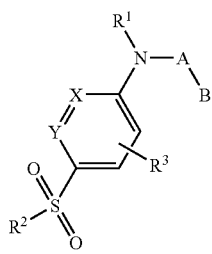

Formula I wherein:

A is $-(CR_2)_n-$ where n is 1, 2, or 3 and R is independently hydrogen or alkyl;

B is aryl or heteroaryl;

X and Y are, independently, CH or nitrogen;

$R^1$ is alkyl, alkenyl, cyanoalkyl, cycloalkyl, cycloalkylalkyl, aryl, aralkyl, heteroaralkyl, heterocyclyl, heterocyclylalkyl, heteroalkyl or alkylcarbonylalkyl;

$R^2$ is alkyl, haloalkyl, cycloalkyl, cycloalkylalkyl, alkenyl, hydroxyalkyl, alkoxyalkyl, alkoxycarbonylalkyl, aryl, aralkyl, or $NR^{13}R^{14}$ wherein $R^{13}$ is hydrogen or alkyl;

$R^{14}$ is hydrogen, alkyl, alkenyl, acyl, haloalkyl, cycloalkyl, cycloalkylalkyl, aralkyl, hydroxyalkyl, alkoxyalkyl, carboxyalkyl, alkoxycarbonylalkyl, or aminoalkyl;

$R^3$ is hydrogen, alkyl, halo, nitro, cyano, hydroxy or alkoxy;

and prodrugs, individual isomers, mixtures of isomers, and pharmaceutically acceptable salts thereof.

In a second aspect, this invention provides pharmaceutical compositions containing a therapeutically effective amount of a compound of formula (I) or its pharmaceutically acceptable salt and a pharmaceutically acceptable excipient.

In a third aspect, this invention provides a method of treatment of a disease, in particular an inflammatory or autoimmune disease, in a mammal treatable by administration of a prostaglandin G/H synthase inhibitor, comprising administration of a therapeutically effective amount of a compound of formula (I) or its pharmaceutically acceptable salt.

In a fourth aspect, this invention provides processes for preparing compounds of formula (I).

DETAILED DESCRIPTION OF THE INVENTION

Definitions

Unless otherwise stated, the following terms used in the specification and claims have the meanings given below:

"Acyl" means the group —C(O)R', where R' is hydrogen, alkyl, cycloalkyl, cycloalkylalkyl, phenyl or phenylalkyl.

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Alkoxycarbonylalkyl" means a radical —R$^a$C(O)R$^b$ where Ra is an alkylene group as defined above and Rb is an alkoxy group as defined above e.g., methoxycarbonylethyl, ethoxycarbonylbutyl, and the like.

"Aryl" means a monovalent monocyclic or bicyclic aromatic hydrocarbon radical of 6 to 10 ring atoms which is substituted independently with one to four substituents, preferably one, two, or three substituents selected from alkyl, cycloalkyl, cycloalkyl-alkyl, halo, nitro, cyano, hydroxy, alkoxy, alkylthio, alkylsulfonyl, amino, acylamino, mono-alkylamino, di-alkylamino, haloalkyl, haloalkoxy, heteroalkyl, COR (where R is hydrogen, alkyl, cycloalkyl, cycloalkylalkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$^n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the derivatives thereof.

"Aralkyl" means a radical —R$^a$R$^b$ where R$^a$ is an alkylene group and R$^b$ is an aryl group as defined herein, e.g., benzyl, phenylethyl, 3-(3-chlorophenyl)-2-methylpentyl, and the like.

"Aralkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group and R$^b$ is an aryl group as defined herein, e.g., 2-hydroxy-2-phenyl-ethyl, 2-hydroxy-1-hydroxymethyl-2-phenyl-ethyl, and the like.

"Cycloalkyl" means a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, acylamino, mono-alkylamino, di-alkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkyl-alkyl" means a radical —R$^a$R$^b$ where R$^a$ is an alkylene group and R$^b$ is a cycloalkyl group as defined herein, e.g., cyclopropylmethyl, cyclohexylpropyl, 3-cyclohexyl-2-methylpropyl, and the like.

"Haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all hydrogen atoms are replaced by fluorine atoms.

"Heteroalkyl" means an alkyl radical as defined herein with one, two or three substituents independently selected from —OR$^a$, —NR$^b$R$^c$, and —S(O)$_n$R$^d$ (where n is an integer from 0 to 2), with the understanding that the point of attachment of the heteroalkyl radical is through a carbon atom of the heteroalkyl radical. R$^a$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. R$^b$ is hydrogen, alkyl, cycloalkyl, cycloalkyl-alkyl, aryl or aralkyl. R$^c$ is hydrogen, alkyl, cycloalkyl, cycloalkyl-alkyl, aryl, aralkyl, acyl, alkoxycarbonyl, aryloxycarbonyl, carboxamido, mono- or di-alkylcarbamoyl or alkylsulfonyl. R$^d$ is hydrogen (provided that n is 0), alkyl, cycloalkyl, cycloalkyl-alkyl, aryl, aralkyl, heteroaryl,amino, mono-alkylamino, di-alkylamino, hydroxyalkyl or hydroxyalkylamino. Representative examples include, for example, 2-hydroxyethyl, 2,3-dihydroxypropyl, 2-methoxyethyl, benzyloxymethyl, 2-methylsulfonyl-ethyl.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl, or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl, or phenylalkyl), or —(CR'R")$_n$—CONR$^a$R$^b$ (where n is an integer from 0 to 5, R' and R" are independently hydrogen or alkyl, and R$^a$ and R$_b$ are, independently of each other, hydrogen, alkyl, cycloalkyl, cycloalkylalkyl, phenyl, or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —R$^a$R$^b$ where R$^a$ is an alkylene group and R$^b$ is a heteroaryl group as defined herein, e.g., pyridin-3-ylmethyl, 3-(benzofuran-2-yl)propyl, and the like.

"Heteroaralkenyl" means a radical —R$^a$R$^b$ where R$^a$ is an alkenylene group and R$^b$ is a heteroaryl group as defined herein, e.g., 3-(pyridin-3-yl)propen-2-yl, and the like.

"Heterocyclyl" means a saturated or unsaturated non-aromatic cyclic radical of 3 to 8 ring atoms in which one or two ring atoms are heteroatoms selected from O, NR (where R is independently hydrogen or alkyl or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —(CR'R")$_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof.

"Heterocyclylalkyl" means a radical —R$^a$R$^b$ where R$^a$ is an alkylene group and R$^b$ is a heterocyclyl group as defined herein, e.g., tetrahydropyran-2-ylmethyl, 4-methylpiperazin-1-ylethyl, 3-piperidinylmethyl, and the like.

"Heteroalkylene" means a linear saturated divalent hydrocarbon radical of one to six carbons or a branched saturated hydrocarbon radical of three to six carbon atoms with one, two or three substituents independently selected from —OR$^a$, —NR$^b$R$^c$, and —S(O)$_n$R$^d$ (where n is an integer from 0 to 2) where, $R^a$, Rb, Rc, and $R^d$ are as defined herein for a heteroalkyl radical. Examples include, 2-hydroxyethan-1,2-diyl, 2-hydroxypropan-1,3-diyl and the like.

"Heterosubstituted cycloalkyl" means a cycloalkyl group wherein one, two, or three hydrogen atoms are replaced by substituents independently selected from the group consisting of hydroxy, alkoxy, amino, acylamino, mono-alkylamino, di-alkylamino, or —$SO_nR$ (where n is an integer from 0 to 2 and when n is 0, R is hydrogen or alkyl and when n is 1 or 2, R is alkyl, cycloalkyl, cycloalkylalkyl, aryl, aralkyl, heteroaryl, amino, acylamino, mon-alkylamino, di-alkylamino, or hydroxyalkyl). Examples include 4-hydroxycyclohexyl, 2-aminocyclohexyl etc.

"Heteroalkylsubstituted cycloalkyl" means a cycloalkyl group wherein one, two, or three hydrogen atoms are replaced independently by heteroalkyl groups, with the understanding that the heteroalkyl group is attached to the cycloalkyl group via a carbon-carbon bond. Examples include 1-hydroxymethyl-cyclopent-1-yl, 2-hydroxymethyl-cyclohex-2-yl and the like.

"Heteroalkylsubstituted heterocyclyl" means a heterocyclyl group wherein one, two, or three hydrogen atoms are replaced independently by heteroalkyl groups, with the understanding that the heteroalkyl group is attached to the heterocyclyl group via a carbon-carbon bond. Examples include 4-hydroxymethyl-piperidin-1-yl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl. Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —$(CR'R'')_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl).

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g. acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in a compound of Formula (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Protecting group" refers to a grouping of atoms that when attached to a reactive group in a molecule masks, reduces or prevents that reactivity. Examples of protecting groups can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or
(3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of "Advanced Organic Chemistry", 4th edition J. March, John Wiley and Sons, New York, 1992).

Nomenclature

The naming and numbering of the compounds of this invention is illustrated below.

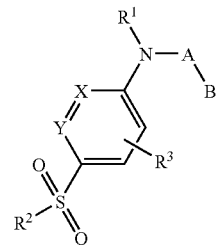

(I)

The nomenclature used in this application is generally based on the IUPAC recommendations, e.g., a compound of formula (I):

where $R^3$ is hydrogen, $R^2$ is methyl, $R^1$ is 2-(methylsulfonyl)ethyl, A is $CH_2$, B is 4-fluorophenyl, X is CH and Y is CH is named 4-{N,N-[2-(methylsulfonyl)ethyl](4-fluorobenzyl)amino}phenyl methyl sulfone.

where $R^3$ is hydrogen, $R^2$ is methyl, $R^1$ is benzyl, A is $CH_2$, B is 4-fluorophenyl, X is CH and Y is CH is named 4-[N,N-(benzyl)(4-fluorobenzyl)amino]phenyl methyl sulfone.

where $R^3$ is hydrogen, $R^2$ is methyl, $R^1$ is 2-(methylsulfonyl)ethyl, A is $CH_2$, B is 4-fluorophenyl, X is nitrogen and Y is CH is named 2-{N,N-[2-(methylsulfonyl)ethyl](4-fluorobenzyl)amino}pyridin-5-yl methyl sulfone.

where $R^3$ is hydrogen, $R^2$ is $NH_2$, $R^1$ is 2-methylsulfonylethyl, A is $CH_2$, B is 4-methyl-phenyl, X is CH and Y is CH is named 4-[(2-methylsulfonyl-ethyl)-(4-methyl-benzyl)-amino]-benzenesulfonamide.

where $R^3$ is 3-fluoro, $R^2$ is methyl, $R^1$ is 2-methylsulfonylethyl, A is $CH_2$, B is 4-ethoxy-phenyl, X is CH and Y is CH is named (4-ethoxy-benzyl)-(3-fluoro-4-methanesulfonylphenyl)-(2-methanesulfonyl-ethyl)-amine.

Representative Compounds of this Invention are as Follows

I. Compounds of Formula (I) Where $R^2$ is $CH_3$ and the Other Groups are Defined as Below:

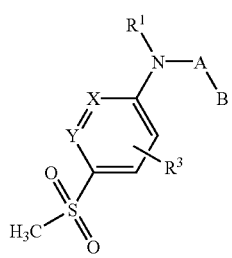

| CPD # | A | B | X | Y | $R^1$ | $R^3$ | Made by Example | M. Pt. ° C. | M/S m/e |
|---|---|---|---|---|---|---|---|---|---|
| 1-1 | $CH_2$ | phenyl | CH | CH | 2-(methylsulfonyl)ethyl | H | 6 | | 367 |
| 1-2 | $CH_2$ | 2-fluorophenyl | CH | CH | 2-(methylsulfonyl)ethyl | H | 6 | | 385 |

-continued

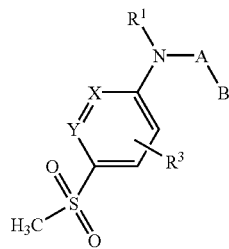

| CPD # | A | B | X | Y | R¹ | R³ | Made by Example | M. Pt. ° C. | M/S m/e |
|---|---|---|---|---|---|---|---|---|---|
| 1-3 | CH₂ | 2-methoxyphenyl | CH | CH | 2-(methylsulfonyl)ethyl | H | 6 | | 397 |
| 1-4 | CH₂ | 3,4-difluorophenyl | CH | CH | 2-(methylsulfonyl)ethyl | H | 6 | | 403 |
| 1-5 | CH₂ | 2-chloro-4-fluorophenyl | CH | CH | 2-(methylsulfonyl)ethyl | H | 6 | | 419 |
| 1-6 | CH₂ | 3,4-dimethylphenyl | CH | CH | 2-(methylsulfonyl)ethyl | H | 6 | | 395 |
| 1-7 | CH₂ | 2,4-dichlorophenyl | CH | CH | 2-(methylsulfonyl)ethyl | H | 6 | | 436 |
| 1-8 | CH₂ | 4-trifluoromethyl phenyl | CH | CH | 2-(methylsulfonyl)ethyl | H | 6 | | 435 |
| 1-9 | CH₂ | 2-bromophenyl | CH | CH | 2-(methylsulfonyl)ethyl | H | 6 | | 446 |
| 1-10 | CH₂ | 3-fluorophenyl | CH | CH | 2-(methylsulfonyl)ethyl | H | 6 | | 385 |
| 1-11 | CH₂ | 3-chlorophenyl | CH | CH | 2-(methylsulfonyl)ethyl | H | 6 | | 401 |
| 1-12 | CH₂ | 4-bromophenyl | CH | CH | 2-(methylsulfonyl)ethyl | H | 6 | | 446 |
| 1-13 | CH₂ | 2,3-difluorophenyl | CH | CH | 2-(methylsulfonyl)ethyl | H | 6 | | 403 |
| 1-14 | CH₂ | 3,5-difluorophenyl | CH | CH | 2-(methylsulfonyl)ethyl | H | 6 | | 403 |
| 1-15 | CH₂ | 4-methoxycarbonylphenyl | CH | CH | 2-(methylsulfonyl)ethyl | H | 6 | | 425 |
| 1-16 | CH₂ | 2,5-difluorophenyl | CH | CH | 2-(methylsulfonyl)ethyl | H | 6 | | 403 |
| 1-17 | CH₂ | 2-methylthiazol-4-yl | CH | CH | 2-(methylsulfonyl)ethyl | H | 6 | | 388 |
| 1-18 | CH₂ | 4-methylthiazol-2-yl | CH | CH | 2-(methylsulfonyl)ethyl | H | 6 | | 388 |
| 1-19 | CH₂ | 2-phenylthiazol-4-yl | CH | CH | 2-(methylsulfonyl)ethyl | H | 6 | | 450 |
| 1-20 | CH₂ | 2-(4-chlorophenyl) thiazol-4-yl | CH | CH | 2-(methylsulfonyl)ethyl | H | 6 | | 485 |
| 1-21 | CH₂ | 4-fluorophenyl | CH | CH | ethyl | H | 2 | | 307 |
| 1-22 | CH₂ | thiophen-2-yl | CH | CH | butyl | H | 3 | | 323 |
| 1-23 | CH₂ | phenyl | CH | CH | butyl | H | 2 | | 317 |
| 1-24 | CH₂ | 4-fluorophenyl | CH | CH | pentyl | H | 2 | | 349 |
| 1-25 | CH₂ | 4-fluorophenyl | CH | CH | isopropyl | H | 2 | | 321 |
| 1-26 | CH₂ | 4-fluorophenyl | CH | CH | propyl | H | E2 | | 321 |
| 1-27 | CH₂ | 4-fluorophenyl | CH | CH | butyl | H | 2 | | 335 |
| 1-28 | CH₂ | 4-fluorophenyl | CH | CH | isoamyl | H | 2 | | 349 |
| 1-29 | CH₂ | 4-fluorophenyl | CH | CH | isobutyl | H | 2 | | 335 |
| 1-30 | CH₂ | 4-fluorophenyl | CH | CH | 2-(methoxy)ethyl | H | 2 | | 337 |
| 1-31 | (CH)CH₃ | phenyl | CH | CH | 2-(methylsulfonyl)ethyl | H | 4 | | 381 |
| 1-32 | CH₂ | 4-fluorophenyl | CH | CH | hydroxypropyl | H | 2 | | 337 |
| 1-33 | CH₂ | 4-fluorophenyl | CH | CH | 3-(methylsulfonyl)propyl | H | 4 | | 399 |
| 1-34 | CH₂ | 4-fluorophenyl | CH | CH | 2-(ethylsulfonyl)ethyl | H | 4 | 109.6–110.7 | 399 |
| 1-35 | CH₂ | 4-fluorophenyl | CH | CH | 2-(methylsulfonyl)ethyl | H | 4 | | 472 |
| 1-36 | CH₂ | 4-fluorophenyl | CH | CH | hydroxyethyl | H | 2 | | 323 |
| 1-37 | CH₂ | 4-fluorophenyl | CH | CH | cyclopropylmethyl | H | 2 | | 333 |
| 1-38 | CH₂ | 4-fluorophenyl | CH | CH | 1-(tertbutoxycarbonyl)-pyrrolidin-3-yl | H | 2 | 174.4–178.0 | 448 |
| 1-39 | CH₂ | 4-fluorophenyl | CH | CH | 2-(morpholin-4-yl)ethyl | H | 2 | | 392 |
| 1-40 | CH₂ | 4-fluorophenyl | CH | CH | pyrrolidin-3-yl | H | 2 | 124.0–124.3 | 348 |
| 1-41 | CH₂ | 4-fluorophenyl | CH | CH | 3-(pyrrolidin-2-on-1-yl)-propyl | H | 2 | | 404 |
| 1-42 | CH₂ | 4-fluorophenyl | CH | CH | benzyl | H | 1 | | 369 |
| 1-43 | CH₂ | 4-fluorophenyl | CH | CH | 2-[N,N-(acetyl)(4-fluorobenzyl)amino]ethyl | H | 2 | | 472 |
| 1-44 | CH₂ | 2,4-difluorophenyl | CH | CH | 2-(methylsulfonyl)ethyl | H | 4 | 149.4–150.4 | 403 |
| 1-45 | CH₂ | pyridin-2-yl | CH | CH | 2-(methylsulfonyl)ethyl | H | 5 | 139.5–140.5 | 368 |
| 1-46 | CH₂ | 4-methoxyphenyl | CH | CH | 2-(methylsulfonyl)ethyl | H | 4 | | 397 |
| 1-47 | CH₂ | 2-chlorophenyl | CH | CH | butyl | H | 2 | | 351 |
| 1-48 | CH₂ | 2-fluorophenyl | CH | CH | butyl | H | 2 | | 335 |
| 1-49 | CH₂ | 2-methoxyphenyl | CH | CH | butyl | H | 2 | | 347 |
| 1-50 | CH₂ | 4-chlorophenyl | CH | CH | butyl | H | 2 | | 351 |
| 1-51 | CH₂ | 4-methoxyphenyl | CH | CH | butyl | H | 2 | | 347 |
| 1-52 | CH₂ | 4-cyanophenyl | CH | CH | butyl | H | 2 | | 342 |
| 1-53 | CH₂ | 2,4-difluorophenyl | CH | CH | butyl | H | 2 | | 353 |
| 1-54 | CH₂ | 3,4-difluorophenyl | CH | CH | butyl | H | 2 | | 353 |
| 1-55 | CH₂ | 4-chlorophenyl | CH | CH | 2-(methylsulfonyl)ethyl | H | 4 | | 401 |
| 1-56 | CH₂ | 2-chlorophenyl | CH | CH | 2-(methylsulfonyl)ethyl | H | 4 | | 401 |
| 1-57 | CH₂ | 6-chloropyridazin-3-yl | CH | CH | 2-(methylsulfonyl)ethyl | H | 5 | | 403 |

-continued

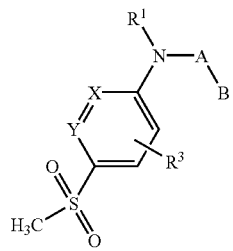

| CPD # | A | B | X | Y | R¹ | R³ | Made by Example | M. Pt. ° C. | M/S m/e |
|---|---|---|---|---|---|---|---|---|---|
| 1-58 | $CH_2$ | 6-oxo-pyridazin-3-yl | CH | CH | 2-(methylsulfonyl)ethyl | H | 5 | | 385 |
| 1-59 | $CH_2$ | benzothiazol-2-yl | CH | CH | 2-(methylsulfonyl)ethyl | H | 5 | | 424 |
| 1-60 | $CH_2$ | 4-fluorophenyl | N | CH | 2-(methylsulfonyl)ethyl | H | 11 | | 386 |
| 1-61 | $CH_2$ | 4-fluorophenyl | CH | N | 2-(methylsulfonyl)ethyl | H | 12 | | 386 |
| 1-62 | $CH_2$ | thiazol-2-yl | CH | CH | 2-(methylsulfonyl)ethyl | H | 6 | | 388 |
| 1-63 | $CH_2$ | 2-methoxypyridin-5-yl | CH | CH | 2-(methylsulfonyl)ethyl | H | 5 | | 398 |
| 1-64 | $CH_2$ | 2-ethoxypyridin-5-yl | CH | CH | 2-(methylsulfonyl)ethyl | H | 5 | | 412 |
| 1-65 | $CH_2$ | 4-ethoxyphenyl | CH | CH | 2-(methylsulfonyl)ethyl | H | 7 | | 411 |
| 1-66 | $CH_2$ | pyridin-3-yl | CH | CH | 2-(methylsulfonyl)ethyl | H | 5 | | 368 |
| 1-67 | $CH_2$ | pyridin-4-yl | CH | CH | 2-(methylsulfonyl)ethyl | H | 5 | 154.4–154.6 | 368 |
| 1-68 | $CH_2$ | 4-fluorophenyl | CH | CH | 4-methylsulfonyl-phenyl | H | 8 | | 433 |
| 1-69 | $CH_2$ | 4-fluorophenyl | CH | CH | 4-methylthio-phenyl | H | 8 | | 401 |
| 1-70 | $CH_2$ | 4-fluorophenyl | CH | CH | 3-oxo-butyl | H | 9 | | 349 |
| 1-71 | $(CH_2)_3$ | phenyl | CH | CH | 2-(methylsulfonyl)ethyl | H | 4 | | 395 |
| 1-72 | $CH_2$ | 4-ethoxyphenyl | CH | CH | 2-(methylsulfonyl)ethyl | 3-F | 13 | 56–59 | 429 |
| 1-73 | $CH_2$ | 4-fluorophenyl | CH | CH | 2-(methylsulfonyl)ethyl | 3-F | 13 | | 403 |
| 1-74 | $CH_2$ | 4-fluorophenyl | CH | CH | 2-(methylsulfonyl)ethyl | 3-OMe | 13 | | 415 |
| 1-75 | $CH_2$ | 4-(methylsulfonyl)phenyl | CH | CH | 2-(methylsulfonyl)ethyl | H | 6 | | 445 |
| 1-76 | $CH_2$ | 4-ethoxyphenyl | CH | CH | 2-(3-thienyl)ethyl | H | 18 | | 401 |
| 1-77 | $CH_2$ | 4-ethoxyphenyl | CH | CH | imidazol-4-ylmethyl | H | 18 | | 385 |
| 1-78 | $CH_2$ | 4-ethoxyphenyl | CH | CH | 2-(methylsulfinyl)ethyl | H | 14 | | 395 |
| 1-79 | $CH_2$ | 4-fluoro-3-hydroxyphenyl | CH | CH | 2-(methylsulfonyl)ethyl | H | 17 | | 401 |
| 1-80 | $CH_2$ | 4-fluorophenyl | CH | CH | 2-(2-hydroxyethylaminosulfonyl)ethyl | H | 5 | | 430 |
| 1-81 | $CH_2$ | 4-fluorophenyl | CH | CH | 2-(imidazol-1-ylsulfonyl)ethyl | H | 5 | | 437 |

II. Compounds of Formula (I) Where X and Y are CH, R³ is Hydrogen and the Other Groups are Defined as Below:

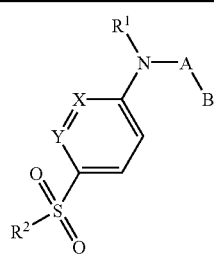

| CPD # | A | B | X | Y | R¹ | R² | Made By Example | M. Pt. ° C | Mass. Spec. m/e |
|---|---|---|---|---|---|---|---|---|---|
| 2-1 | $CH_2$ | 4-methyl-phenyl | CH | CH | 24 2-(methylsulfonyl)ethyl | 4-methoxy-benzylamino | 10 | 85.7–86.6 | 502 |
| 2-2 | $CH_2$ | 4-methyl-phenyl | CH | CH | 2-(methylsulfonyl)ethyl | $NH_2$ | 10 | 169.1–170.0 | 385 |
| 2-3 | $CH_2$ | 4-fluorophenyl | CH | CH | 2-(methylsulfonyl)ethyl | $NH_2$ | 10 | | 386 |
| 2-4 | $CH_2$ | 2,4-difluoro-phenyl | CH | CH | 2-(methylsulfonyl)ethyl | $NH_2$ | 10 | 152.9–153.2 | 404 |
| 2-5 | $CH_2$ | 4-fluoro-phenyl | CH | CH | 2-(methylthio)ethyl | $NH_2$ | 14 | | 355 |
| 2-6 | $CH_2$ | 4-ethoxyphenyl | CH | CH | 2-(methylsulfonyl)ethyl | $NH_2$ | 14 | | 413 |
| 2-7 | $CH_2$ | 2-fluorophenyl | CH | CH | 2-(methylsulfonyl)ethyl | $NH_2$ | 14 | | 387 |
| 2-8 | $CH_2$ | 2,6-difluorophenyl | CH | CH | 2-(methylsulfonyl)ethyl | $NH_2$ | 14 | | 405 |
| 2-9 | $CH_2$ | 2-methoxyphenyl | CH | CH | 2-(methylsulfonyl)ethyl | $NH_2$ | 14 | | 399 |
| 2-10 | $CH_2$ | 2-chlorophenyl | CH | CH | 2-(methylsulfonyl)ethyl | $NH_2$ | 14 | | 403 |

-continued

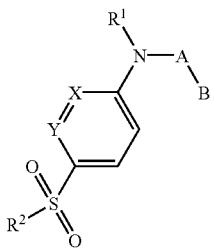

| CPD # | A | B | X | Y | R¹ | R² | Made By Example | M. Pt. °C | Mass. Spec. m/e |
|---|---|---|---|---|---|---|---|---|---|
| 2-11 | $CH_2$ | 2-fluorophenyl | CH | CH | 2-(methylsulfonyl)ethyl | 2-fluoro benzylamino | 16 | | 495 |
| 2-12 | $CH_2$ | 4-fluorophenyl | CH | CH | 2-(methylsulfonyl)ethyl | ethylamino | 15 | | 415 |

PREFERRED EMBODIMENTS

While the broadest definition of this invention is set forth in the Summary of the Invention, certain compounds of Formula (I) are preferred.

In certain preferred embodiments, $R^3$ is hydrogen.

In certain preferred embodiments, A is —$CH_2$—, $CH_2$—$CH_2$— or —$CH(CH_3)$—; preferably —$CH_2$—.

In certain preferred embodiments, X is CH and Y is CH.

In other preferred embodiments, X is N and Y is CH.

In other preferred embodiments, X is CH and Y is N.

In certain preferred embodiments, B is aryl, preferably optionally substituted phenyl.

In other preferred embodiments, B is heteroaryl, preferably furyl, imidazolyl, pyridyl, thienyl, thiazolyl, benzothiazolyl or pyridazinyl.

In certain preferred embodiments $R^1$ is alkyl, cycloalkyl, cycloalkyl-alkyl, heterocyclyl, heterocyclylalkyl or heteroalkyl; more preferably heteroalkyl, especially alkylsulfonyl-alkyl (e.g. 2-methylsulfonyl-ethyl).

In certain preferred embodiments $R^2$ is alkyl, more preferably methyl.

In other preferred embodiments $R^2$ is $NH_2$.

A particularly preferred group is (II) where X and Y are CH.

Within this group, in one preferred embodiment, B is phenyl optionally substituted from the group consisting of halo, alkoxy, and cyano, especially mono-substituted with fluoro (e.g. 4-fluorophenyl); $R^1$ is alkylsulfonyl-ethyl, particularly 2-methylsulfonyl-ethyl; and $R^2$ is alkyl, particularly methyl or $NH_2$.

In another preferred group within (II), B is heteroaryl, preferably furyl, imidazolyl, pyridyl, thienyl, thiazolyl, benzothiazolyl or pyridazinyl; $R^1$ is alkylsulfonylethyl, particularly 2-methylsulfonyl-ethyl; and $R^2$ is alkyl, particularly methyl, or $NH_2$.

A number of different substituent preferences have been given above and following any of these substituent preferences results in a compound of the invention that is more preferred than one in which the particular substituent preference is not followed. However, these substituent preferences are generally independent, although some preferences are mutually exclusive, and following more than one of these preferences may result in a more preferred compound than one in which fewer of the substituent preferences are followed.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.), Lancaster Synthesis (Pelham, N.C.), Maybridge Chemical Co. LTD (Cornwall, United Kingdom) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989); *Organic Reactions*, Volumes 1–40 (John Wiley and Sons, 1991), *March's Advanced Organic Chemistry*, (John Wiley and Sons, 4th Edition) and *Larock's Comprehensive Organic Transformations* (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Preparation of Compounds of Formula (I)

Schemes A–F describe methods to generate the compounds of Formula (I). One of skill in the art will recognize that groups $R^1$, $R^2$, $R^3$, A and B may be present in protected form at any point in the Schemes and will be removed at the appropriate juncture.

Scheme A describes the synthesis of a compound of formula (I) wherein X and Y are CH and $R^1$, $R^2$, $R^3$, A, and B are as defined in the Summary of the Invention.

Scheme A

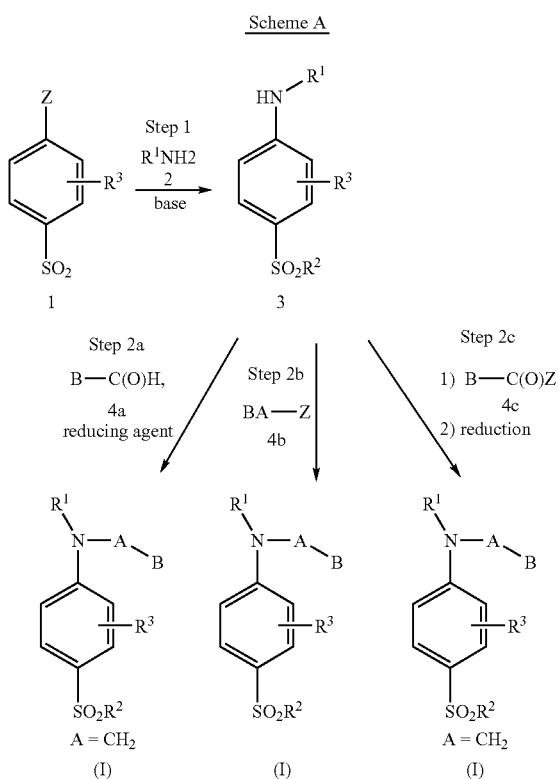

In Step 1, reaction of a phenylsulfonyl compound of formula 1 (where Z is an appropriate leaving group such as fluoro or bromo) with a monosubstituted amine of formula 2 (wherein $R^1$ is as defined in the Summary of the Invention or a protected precursor thereof) gives a 4-aminophenylsulfonyl compound of formula 3. The reaction is carried out at elevated temperature, preferably in the range of 50–80° C. and in the presence of a base such as potassium carbonate, triethylamine, and the like. Suitable solvents for the reaction are polar aprotic solvents such as DMF, DMSO, HMPA, and the like. In general, the compounds of formula 1 are commercially available or can be readily synthesized by those of ordinary skill in the art.

Compounds of formula (I) can be prepared from a compound of formula 3 by any of the following three steps: Step 2a, 2b, or 2c.

As shown in Step 2a, a compound of formula (I) can be prepared from a compound of formula 3 by reductive amination. Reaction of compound 3 with an aldehyde of formula 4a (wherein B is as defined in the Summary of the Invention or a protected precursor thereof) and a suitable reducing agent (e.g. a hydride reducing agent such as $NaBH(OAc)_3$) gives a compound of Formula (I) (wherein A is $CH_2$). Suitable solvents for the reaction are halogenated hydrocarbons, such as dichloromethane, dichloroethane, and the like. See, for example, Example 3.

Alternatively, as shown in Step 2b, a compound of formula (I) can be prepared from a compound of formula 3 by direct nucleophilic alkylation. Reaction of compound 3 with a compound of formula 4b (where B and A are defined in the Summary of the Invention or a protected precursor thereof and Z is an appropriate leaving group such as bromo and chloro) gives a compound of formula (I). The reaction is carried out in the presence of a base such as sodium hydride. Suitable solvents for the reaction are polar aprotic solvents such as DMF, DMSO, HMPA, and the like. This reaction is carried out at approximately room temperature to 70° C. See, for example, Examples 2 and 4.

Alternatively, as shown in Step 2c, a compound of formula (I) can be prepared from a compound of formula 3 by acylation/reduction. Compound 3 is reacted with an acid chloride or carboxylic acid of formula 4c (where Z is a leaving group, such as chloro or —OH and B is as defined in the Summary of the Invention or a protected precursor thereof). If the compound of formula 4c is a carboxylic acid a coupling agent, such as DCC, must also be present. This acylation is followed by reduction using a suitable reducing agent (typically a hydride reducing agent such as LAH, $B_2H_6$, $BH_3DMS$, and the like) to provide a compound of formula (I) (wherein A is $CH_2$) Suitable solvents for the reaction are polar, anhydrous solvents such as THF, ether, and the like.

Additional steps may be added to this general Scheme A as necessary to provide the desired compound of formula (I). As an example of an additional step, it may be necessary to protect functional groups in $R^1$ of compound 3 before preparing a compound of formula (I) by Step 2a, 2b, or 2c and then subsequently deprotect the functional group. For example, amine functionality in a compound of formula 3, may be protected by treatment of 3 with di-tert-butyl dicarbonate, followed by removal of the tert-butyloxy carbonyl protecting group after Step 2. Examples of protecting groups and their synthetic use can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). These protection/deprotection steps are well known by those of ordinary skill in the art and need not be further elaborated.

Compounds of formula (I) may also be obtained by further modification of a functional group on a compound of formula (I). For example, compounds of formula (I), where $R^1$ is alkylsulfonylalkyl (e.g. methylsulfonyl ethyl) may be obtained by oxidation of the corresponding alkylthioalkyl compound which in turn may be prepared via step 1 by treating a compound of formula 1 with the corresponding alkylthioalkyl amine.

Scheme B describes an alternative synthesis of a compound of formula (1) by sequential alkylation of an aromatic amine, 5, wherein X, Y, $R^1$, $R^2$, $R^3$, A and B are as defined in the Summary of the Invention or protected precursors thereof, except that $R^2$ is not $NR^{13}R^{14}$

Scheme B

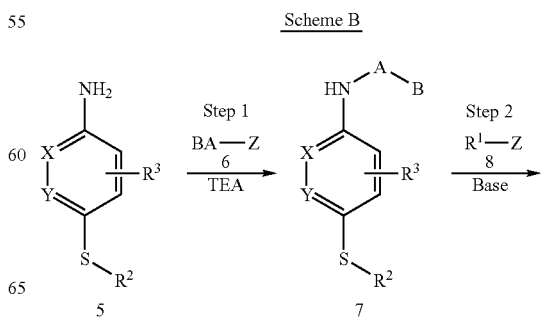

Scheme C

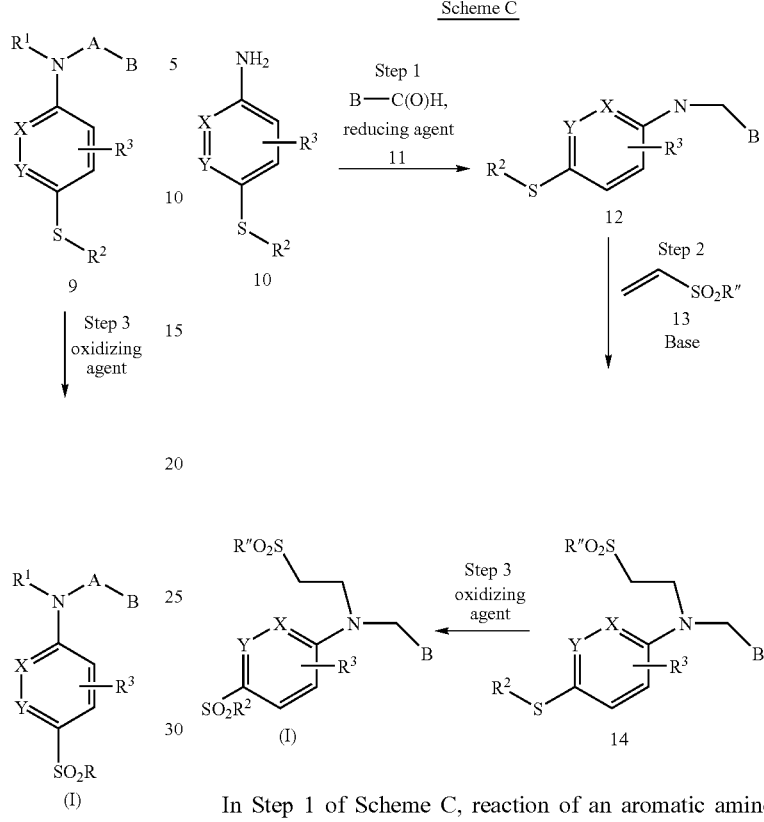

In Step 1, reaction of an aromatic amine of formula 5 with a nucleophilic alkylating agent of formula 6 (where B and A are as defined in the Summary of the Invention or a protected precursor thereof and Z is an appropriate leaving group such as bromo, and chloro) in the presence of a base (such as triethylamine (TEA) or diisopropylethyl amine) provides a compound of formula 7. Suitable solvents for this reaction are dichloromethane, THF, and the like.

In Step 2, a compound of formula 7 is reacted with an alkylating agent of formula 8 (wherein $R^1$ is as defined in the Summary of the Invention and Z is an appropriate leaving group such as bromo and chloro) to provide a compound of formula 9. The reaction is carried out in the presence of a base such as sodium hydride. Suitable solvents for the reaction are polar, aprotic solvents such as DMF, DMSO, HMPA, and the like.

In Step 3, oxidation of a compound of formula 9 with a suitable oxidizing agent, such as potassium peroxymonosulfate (OXONE™), MCPBA, and the like, provides a compound of formula (I). Suitable solvents for the reaction are alcohols, such as methanol and ethanol. See, for example, Example 1.

Scheme C describes the synthesis of a compound of formula (I) wherein X, Y, $R^2$, $R^3$ and B are as defined in the Summary of the Invention (except that $R^2$ is not $NR^{13}R^{14}$), A is —$CH_2$— and $R^1$ is alkylsulfonylalkyl.

In Step 1 of Scheme C, reaction of an aromatic amine sulfide of formula 10 with an aldehyde of formula 11 and a suitable reducing agent (such as $NaBH(OAc)_3$) gives an amino substituted aromatic sulfide of formula 12.

In Step 2, an aromatic sulfide of formula 12 is reacted with a vinyl sulfone of formula 13 in the presence of a base such as sodium hydride to provide a sulfide of formula 14. Suitable solvents for the reaction are polar aprotic solvents such as DMF, DMSO, HMPA, and the like In Step 3, oxidation of a sulfide of formula 14 with a suitable oxidizing agent, such as potassium peroxymonosulfate (OXONE™), MCPBA, and the like, provides a compound of formula (I). Suitable solvents for the reaction are alcohols, such as methanol and ethanol. See, for example, Example 5.

4-anilino sulfides of formula 10 where X and Y are both CH are available from commercial suppliers such as Aldrich Chemical Co. Amino-pyridyl sulfides and amino-pyridazinyl sulfides of formula 10, where either of X and Y are N may be prepared from the corresponding amino-pyridines and amino-pyridazines by halogenation and alkylation with a thiolate as shown in Scheme C1.

Scheme C1

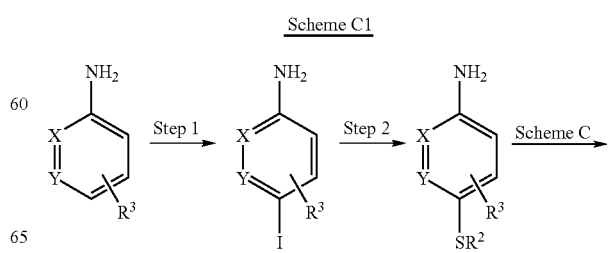

In Step 1, the heteroaromatic amine is treated with $I_2$ in DMSO as described in *Heterocycles* 1984, 1195 to give an iodinated product that is treated with $NaSR_2$ in DMF in Step 2 to displace the iodine to form a compound of formula 10 which is carried forward into Scheme C.

Alternatively, compounds of formula 10 where either of X and Y are N may also be prepared by thiolation of the corresponding halo nitro heteroaromatic compounds followed by reduction of the nitro group to an amine as shown in Scheme C2.

Scheme C2

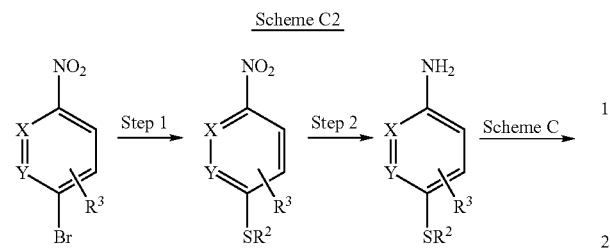

In Step 1, a bromo-nitro-heteroaromatic compound is treated with $NaSR_2$ in DMF to displace the bromine to form the corresponding heteroaromatic sulfide. The sulfide is treated with $TiCl_3$ in acetone and $NH_4OAc$ as described in *Chem. Soc. Perkin. Trans. I.* 1990, 673 to give a compound of formula 10 that is carried forward into Scheme C.

Intermediates of formula 12 from Scheme C may also be alkylated with an alkylating agent, $R^1$-Z, or reductively aminated with an aldehyde, RCHO, as shown in Scheme D to furnish corresponding compounds of Formula I after oxidation.

Scheme D

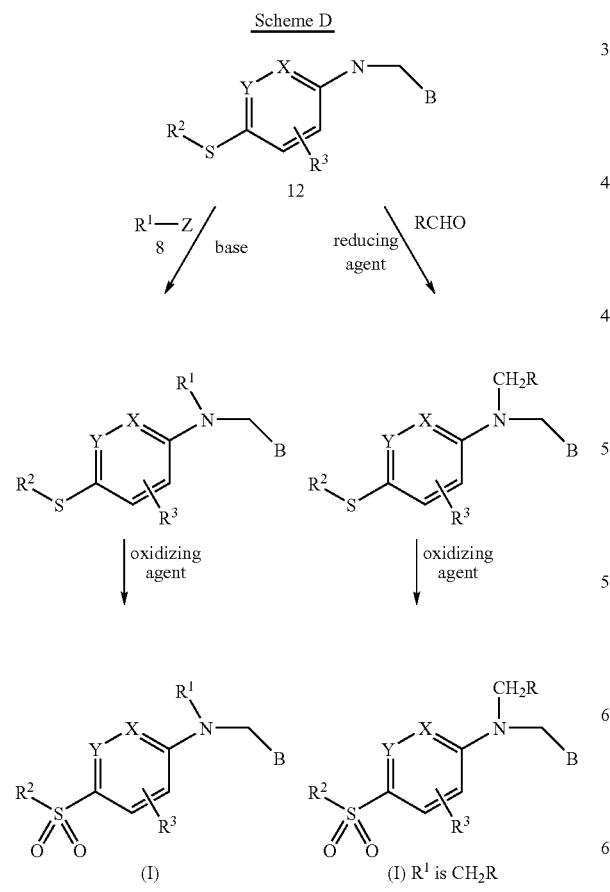

Scheme E describes an alternative synthesis of a compound of formula (I) wherein X and Y are CH, $R^2$ is alkylsulfonylalkyl and $R^1$, $R^3$, A, and B are as defined in the Summary of the Invention, wherein the alkylsulfonylalkyl group is introduced before the introduction of the A-B group.

Scheme E

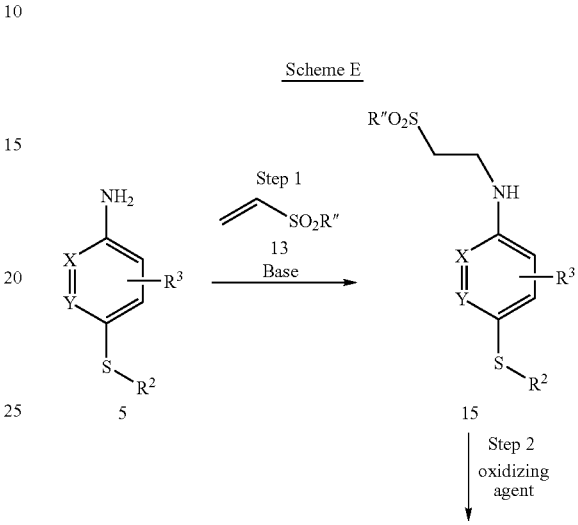

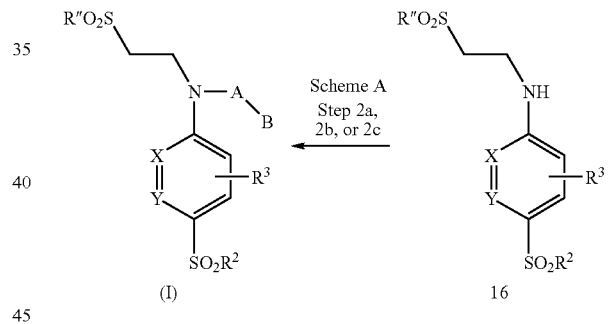

In Step 1, reaction of a compound of formula 5 with a vinyl sulfone of formula 13 in the presence of a base such as sodium hydride provides a compound of formula 15. Suitable solvents for the reaction are polar aprotic solvents such as DMF, DMSO, HMPA, and the like.

In Step 2, oxidation of a compound of formula 15 with a suitable oxidizing agent, such as such as potassium peroxymonosulfate (OXONE™), MCPBA, and the like, provides a sulfone of formula 16. Suitable solvents for the reaction are alcohols, such as methanol and ethanol.

Compounds of formula 16 may be converted to compounds of formula (I) by following Scheme A: Steps 2a, 2b, or 2c above.

Compounds where $R^2$ is $NH_2$ may be prepared by the sequence shown in Scheme F.

Scheme F

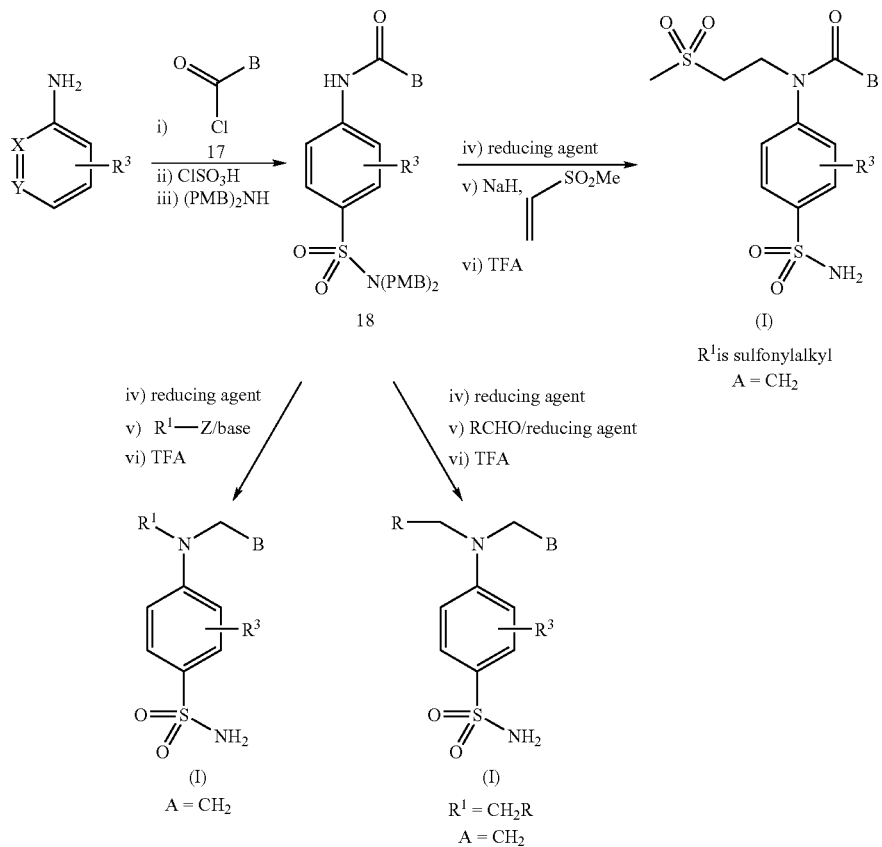

In step i) a compound of formula 5 is acylated with an acid chloride of formula 17 to give an amide that is chlorosulfonylated and aminated with bis(p-methoxybenzyl)amine (PMB) steps ii) and iii) to give a benzene sulfonamide of formula 18.

In step iv), reduction of the amide in 18 gives an amine which is then subsequently elaborated in steps v) and vi) by alkylation with a vinyl sulfone to give a compound of formula (I) where $R^1$ is 2-alkylsulfonyl-ethyl, or by alkylation with $R^1$-Z or by reductive amination with an aldehyde RCHO as described earlier.

Additional compounds where $R^2$ is $NR^{13}R^{14}$ or $NH_2$ or may be prepared by Schemes G and H respectively as shown below.

Scheme G

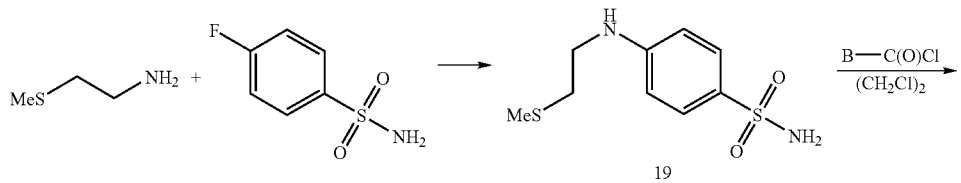

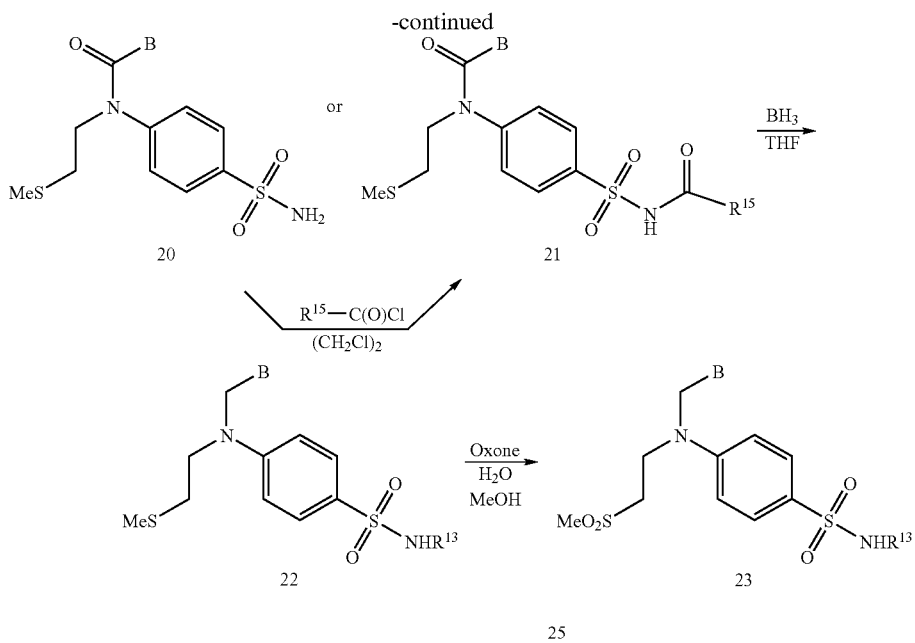

Acylation of a para-methylthioethylamino sulfonamide 19 in the absence of base with an acylating agent BC(O)Cl in an inert solvent provides the monoacylated intermediate 20. Subsequent acylation of the sulfonamido group of 20 provides the bisacylated product 21, which is then reduced to give intermediate 22. Oxidation then provides 23, i.e., compounds Formula I where $A=CH_2$ and $R^2=NHR^{13}$ ($R^{13}$ is alkyl).

Scheme H

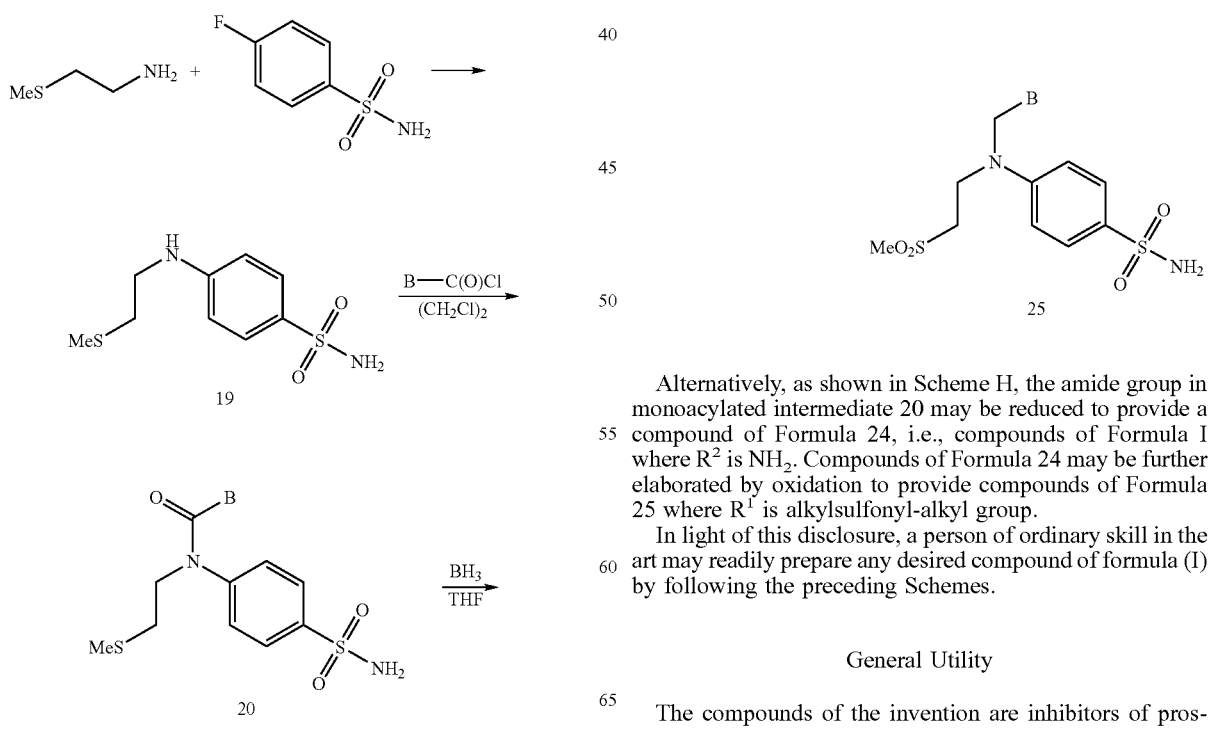

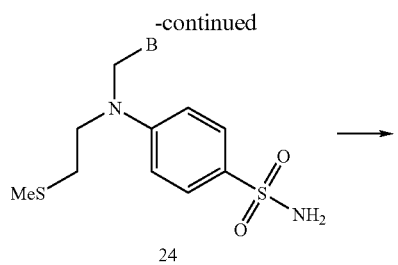

Alternatively, as shown in Scheme H, the amide group in monoacylated intermediate 20 may be reduced to provide a compound of Formula 24, i.e., compounds of Formula I where $R^2$ is $NH_2$. Compounds of Formula 24 may be further elaborated by oxidation to provide compounds of Formula 25 where $R^1$ is alkylsulfonyl-alkyl group.

In light of this disclosure, a person of ordinary skill in the art may readily prepare any desired compound of formula (I) by following the preceding Schemes.

General Utility

The compounds of the invention are inhibitors of prostaglandin G/H Synthase I and II (COX I and COX II), especially COX II, in vitro, and as such are expected to possess both anti-inflammatory and analgesic properties in vivo. See, for example, Goodman and Gilmans's "The Pharmacological Basis of Therapeutics", Ninth Edition, McGraw Hill, New York, 1996, Chapter 27. The compounds, and compositions containing them, are therefore useful as anti-inflammatory and analgesic agents in mammals, especially humans. They find utility in the treatment of fever, inflammation and pain caused by conditions such as rheumatic fever, symptoms associated with influenza or other viral infections, low back and neck pain, dysmenorrhoea, headache, toothache, sprains, myositis, synovitis, arthritis (rheumatoid arthritis and osteoarthritis), gout, ankylosing spondylitis, bursitis, bums or injuries. They maybe used to inhibit prostanoid-induced smooth muscle contractions (e.g., in the treatment of dysmenorrhoea, premature labor and asthma) and to treat autoimmune disorders (such as systemic lupus erythematosus and type I diabetes).

As inhibitors of prostaglandin G/H Synthase, the compounds of this invention are also expected to be useful in the prevention and treatment of cancer, in particular colon cancer. It has been shown that COX-2 gene expression is upregulated in human colorectal cancers and that drugs that inhibit prostaglandin G/H Synthase are effective in animal models of cancer (Eberhart, C. E., et. al., *Gastroenterology*, 107, 1183–1188, (1994), and Ara, G. and Teicher, B. A., *Prostaglandins, Leukotrienes and Essential Fatty Acids*, 54, 3–16, (1996)). In addition, there is epidemiological evidence that shows a correlation between use of drugs that inhibit prostaglandin G/H synthase and a reduced risk of developing colorectal cancer, (Heath, C. W. Jr., et. al., *Cancer*, 74, No. 10, 2885–8, (1994)).

The compounds of this invention are also expected to be useful in the prevention and treatment of Alzheimer's disease. Indomethacin, an inhibitor of prostaglandin G/H synthase, has been shown to inhibit the cognitive decline of Alzheimer's patients, (Rogers, J., et. al., *Neurology*, 43, 1609, (1993)). Also, the use of drugs which inhibit prostaglandin G/H synthase has been linked epidemiologically with a delayed onset of Alzheimer's disease, (Breitner, J. C. S., et. al., *Neurobiology of Aging*, 16, No. 4, 523, (1995) and *Neurology*, 44, 2073, (1994)).

Testing

The anti-inflammatory activity of the compounds of this invention may be assayed by measuring the ability of the compound to inhibit COX I and COX II, especially COX II, in vitro, using a radiometric assay, as described in more detail in Example 9. It may also be assayed by in vivo assays such as the Rat Carrageenan Paw and Rat Air-Pouch assays, as described in more detail in Examples 10 and 11. The analgesic activity of the compounds of this invention may be assayed by in vivo assays such as the Randall-Selitto assay and the rat arthritis pain model, as described in Example 12.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of formula (I) may range from approximately 0.05–35 mg per kilogram body weight of the recipient per day, preferably about 0.15–7 mg/kg/day, most preferably about 0.35 mg/kg/day to 3 mg/kg/day. Thus, for administration to a 70 kg person, the dosage range would preferably be about 10.5 mg to 500 mg per day, most preferably about 25 mg to 200 mg per day.

In light of this disclosure, a person of ordinary skill in the art will have no difficulty in determining what a therapeutically effective amount is.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of formula (I) based on the total formulation, with the balance being one or more suitable pharmaceutical excipients. Preferably, the compound is present at a level of about 1–80 wt %. Representative pharmaceutical formulations containing a compound of formula (I) are described in Example 8.

A person of ordinary skill in the art will have no difficulty, having regard to that skill and this disclosure in determining how to make a suitable formulation.

EXAMPLES

The following preparations and examples are given to enable those skilled in the art to more clearly understand and to practice the present invention. They should not be considered as limiting the scope of the invention, but merely as being illustrative and representative thereof.

Abbreviations used in the examples are defined as follows: "HCl" for hydrochloric acid, "DMF" for dimethylformamide, "NaOH" for sodium hydroxide, "DMSO" for dimethylsulfoxide, "THF" for tetrahydrofuran, "BINAP" for 2,2'-bis(diphenylphosphino)-1,1'-binaphthyl.

Example 1

Synthesis of 4-[N,N-(benzyl)(4-fluorobenzyl)amino]phenyl methyl sulfone (1-42)

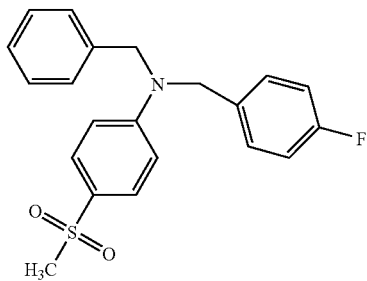

Step 1

To 5.0 mL (40.19 mmol) of 4-(methylthio)aniline and 8.4 mL (60.28 mmol) triethylamine dissloved in 30 mL dichloromethane was added 5.0 mL (40.19 mmol) 4-fluorobenzyl bromide. The mixture was stirred at room temperature for 12 h, partitioned between dichloromethane and sat. aqueous ammonium chloride, dried over MgSO$_4$ and concentrated. Purification by column chromatography, eluting with ethyl acetate/hexane, provided 3.10 g of 4-[(4-fluorobenzyl)amino]thioanisole, along with recovered starting material.

Step 2

100 mg (0.40 mmol) of 4-[(4-fluorobenzyl)amino]thioanisole was dissolved in 2 mL of DMF, to which 76 mg (0.44 mmol) of benzyl bromide was added, followed by 19 mg (0.80 mmol) of NaH. The mixture was warmed to 50° C. and stirred 48 h, quenched with water and concentrated. The residue was partitioned between ethyl acetate and water, dried over MgSO$_4$ and concentrated to provide 70 mg (0.207 mmol) of crude 4-[N,N-(benzyl)(4-fluorobenzyl)amino]thioanisole.

Step 3

The crude 4-[N,N-(benzyl)(4-fluorobenzyl)amino]thioanisole was dissolved in 1.5 mL of methanol, to which 254 mg (0.414 mmol) of OXONE™ was added. The reaction was stirred at room temperature for 12 h, partitioned between ethyl acetate and water, dried over MgSO$_4$ and concentrated to provide 36 mg of 4[N,N-(benzyl)(4-fluorobenzyl)amino]phenyl methyl sulfone.

Example 2

Synthesis of 4-[N,N-(pyrolidin-3-yl)(4-fluorobenzyl)amino]phenyl methyl sulfone (1-40)

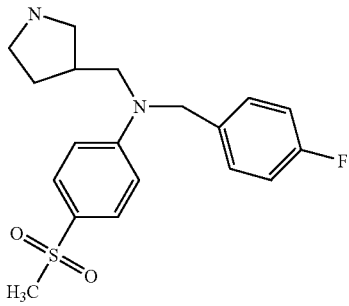

Step 1

To 500 mg (2.87 mmol) 4-fluorophenyl methyl sulfone dissolved in 4 mL DMF was added 247 mg (2.87 mmol) 3-aminopyrrolidine followed by 793 mg (5.74 mmol) potassium carbonate. The mixture was heated to 70° C. and stirred for 48 h. Upon cooling to room temperature, the mixture was partitioned between EtOAc and water, dried over MgSO$_4$ and concentrated to provide 708 mg of 4-(pyrrolidin-3-ylamino)phenyl methyl sulfone, pure by $^1$H NMR.

Step 2

4-(pyrrolidin-3-ylamino)phenyl methyl sulfone (2.96 mmol) was dissolved in 5 mL of THF, to which 645 mg (2.96 mmol) di-tert butyl dicarbonate was added. After 1 h, the mixture was partitioned between EtOAc and water, dried over MgSO$_4$, concentrated and the product crystallized from dichloromethane/hexane to provide 461 mg of 4-(N-BOC-pyrrolidin-3-ylamino)phenyl methyl sulfone, pure by $^1$H NMR.

Step 3

4-(N-BOC-pyrrolidin-3-ylamino)phenyl methyl sulfone (1.35 mmol) was dissolved in 4 mL of DMF, to which 168 μL (1.35 mmol) of 4-fluorobenzyl bromide was added, followed by 62 mg (2.70 mmol) of NaH. The mixture was warmed to 70° C. and stirred 48 h, then quenched with water, partitioned between ethyl acetate and water, dried over MgSO$_4$ and concentrated. The product was crystallized from dichloromethane/hexane to provide 380 mg of 4-[N,N-(N-BOC-pyrrolidin-3-yl)(4-fluorobenzyl)amino]phenyl methyl sulfone, pure by $^1$H NMR; mp 174.4–178.0° C. Anal. Calcd. For C$_{23}$H$_{29}$FN$_2$O$_4$S0.5H$_2$O C, 60.37; H, 6.61; N, 6.12. Found C, 60.61; H, 6.40; N, 6.34. (38).

To 200 mg (0.45 mmol) of 4-[N,N-(N-BOC-pyrrolidin-3-yl)(4-fluorobenzyl)amino]phenyl methyl sulfone dissolved in 5 mL of dichloromethane was added 2 mL of trifluoroacetic acid. The reaction was stirred at room temperature for 3 h, partitioned between dichloromethane and aqueous saturated NaHCO$_3$, was dried over MgSO$_4$ and concentrated to provide 148 mg of 4-[N,N-(pyrrolidin-3-yl)(4-fluorobenzyl)amino]phenyl methyl sulfone, pure by $^1$H NMR, mp 124.0–124.3° C. Anal. Calcd. For C$_{18}$H$_{21}$FN$_2$O$_2$S C, 62.05; H, 6.07; N, 8.04. Found C, 61.29; H, 6.00; N, 7.92. (40)

Following the procedure of Example 1, but replacing 3-aminopyrrolidine in Step 1 with the appropriate amine gave the compounds #24–30, 32, 36–37 and 39–41 of Table 1.

Following the procedure of Example 1, but replacing 3-aminopyrrolidine in Step 1 with n-butylamine and replacing 4-fluorobenzyl bromide in Step 3 with the appropriate aralkyl bromide gave the compounds #47–54 of Table 1.

Example 3

Synthesis of 4-[N,N-(butyl)(thiophen-2-ylmethyl) amino]phenyl methyl sulfone (1-22)

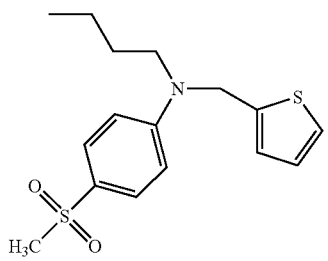

Step 1

To 1.0 g (5.74 mmol) 4-fluorophenyl methyl sulfone dissolved in 5 mL DMF was added 840 μL (11.48 mmol) butylamine followed by 873 mg (6.31 mmol) potassium carbonate. The mixture was heated to 60° C. and stirred for 48 h. Upon cooling to room temperature, the mixture was partitioned between EtOAc and water, dried over $MgSO_4$ and concentrated. Purification by column chromatography, eluting with dichloromethane/hexane, provided 600 mg product 4-(butylamino)phenyl methyl sulfone, pure by $^1H$ NMR.

Step 2

To 250 mg (1.1 mmol) of 4-(butylamino)phenyl methyl sulfone and 103 μL 2-thiophenecarboxaldehyde dissolved in 5 mL dichloromethane was added 350 mg (1.65 mmol) sodium triacetoxyborohydride, followed by 50 μL of acetic acid. The reaction mixture was stirred at room temperature for 12 h. The mixture was then partitioned between ethyl acetate and brine, dried over $MgSO_4$ and concentrated. Purification by HPLC chromatography provided 58 mg of 4-[N,N-(butyl)(thiophen-2-ylmethyl)amino]phenyl methyl sulfone (22).

Example 4

Synthesis of 4-{N,N-[2-(methylsulfonyl)ethyl](4-fluorobenzyl)amino}phenyl methyl sulfone (1-35)

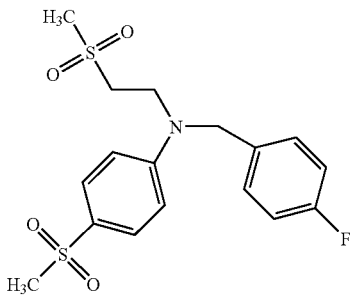

Step 1

To 8.28 g (47.52 mmol) of 4-fluorophenyl methyl sulfone dissloved in 20 mL DMF was added 5.20 g (57.03 mmol) of 2-(methylthio)ethyl amine (1.2 eq.), followed by 13.13 g (95.04 mmol, 2 eq.) potassium carbonate. The mixture was heated to 65° C. and stirred for 12 h. Upon cooling to room temperature, the mixture was partitioned between EtOAc and brine, dried over $MgSO_4$ and concentrated. Column chromatography, eluting with ethyl acetate/hexane, provided 5.53 g of 4-[2-(methylthio)ethylamino]phenyl methyl sulfone, pure by $^1H$ NMR.

Step 2

To 2.5 g of 4-[2-(methylthio)ethylamino]phenyl methyl sulfone (10.19 mmol) dissolved in 10 mL DMF was added 1.26 mL (10.19 mmol) of 4-fluorobenzyl bromide and 468 mg (20.38 mmol) of NaH. After stirring 1 h at room temperature, the reaction was quenched with water and partitioned between EtOAc and water, dried over $MgSO_4$ and concentrated. Purification by column chromatography, eluting with ethyl acetate/hexane, provided 2.44 g product 4-[N,N-(methylthioethyl)(4-fluorobenzyl)amino/phenyl methyl sulfone, pure by $^1H$ NMR.

Step 3

To 2.44 g (6.91 mmol) of 4-{N,N-[2-(methylthio)ethyl](4-fluorobenzyl)amino}phenyl methyl sulfone dissolved in 40 mL MeOH was added 8.5 g (13.83 mmol) OXONE™, followed by slow addition of 5 mL $H_2O$. After stirring at room temperature for 7 h, the mixture was partitioned between EtOAc and water, dried over $MgSO_4$ and concentrated. The product was crystallized from $CH_2Cl_2$ to obtain 600 mg of 4-{N,N-[2-(methylsulfonyl)ethyl](4-fluorobenzyl)amino}phenyl methyl sulfone, pure by $^1H$ NMR, mp 168.6–172.7° C.

Following the procedure of Example 4, but replacing 2-(methylthio)ethyl amine in step 1 with 2-(ethylthio)ethyl amine gave 4-{N,N-[2-(ethylsulfonyl)ethyl](4-fluorobenzyl)amino}phenyl methyl sulfone. Mp. 109.6–110.7° C. Anal. Calcd. For $C_{18}H_{22}FNO_4S_2$ C, 54.12; H, 5.55; N, 3.51. Found C, 53.72; H, 5.48; N, 3.58. (34)

Following the procedure of Example 4, but replacing 4-fluorobenzyl bromide in Step 3 with 2,4-difluorobenzyl bromide gave 4-{N,N-[2-(methylsulfonyl)ethyl](2,4-difluorobenzyl)amino}phenyl methyl sulfone. Mpt. 149.4–150.4° C. Anal. Calcd. For $C_{17}H_{19}F_2NO_4S_2.0.25H_2O$ C, 50.05; H, 4.82; N, 3.43. Found C, 50.04; H, 4.63; N, 3.45. (44)

Example 5

Synthesis of 4-{N,N-[2-(methylsulfonyl)ethyl](pyridin-2-ylmethyl)amino}phenyl methyl sulfone (1-45)

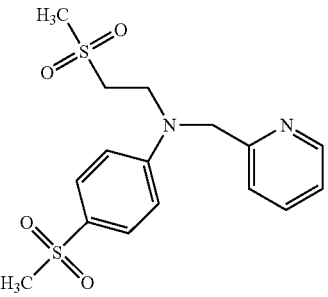

Step 1

To 2.0 mL (16.07 mmol) of 4-(methylthio)aniline dissolved in 25 mL dichloromethane was added 1.52 mL (16.07 mmol) 3-pyridinecarboxaldehyde, followed by 5.11 g (24.11 mmol) sodium triacetoxyborohydride. The mixture was stirred at room temperature for 4 h, partitioned between EtOAc and brine, dried over $MgSO_4$ and concentrated. Column chromatography, eluting with ethyl acetate/hexane, provided 3.70 g of 4-[(pyridin-2-ylmethyl)amino]thioanisole, pure by $^1H$ NMR.

Step 2

To 500 mg (2.17 mmol) of 4-[(pyridin-2-ylmethyl)amino]thioanisole, dissolved in 10 mL N,N-dimethylformamide, was added 230 mg (2.17 mmol) methyl vinyl sulfone followed by 50 mg (2.17 mmol) sodium hydride. The mixture was stirred at room temperature for 0.5 h, partitioned between EtOAc and brine, dried over $MgSO_4$ and concentrated. Crude 4-{N,N-[2-(methylsulfonyl)ethyl](pyridin-2-ylmethyl)amino}thioanisole was obtained in 98% yield (730 mg) and was pure by $^1H$ NMR.

Step 3

To 718 mg (2.13 mmol) of 4-{N,N-[2-(methylsulfonyl)ethyl](pyridin-2-ylmethyl)amino} thioanisole dissolved in 10 mL methanol was added 2.62 g (4.27 mmol) oxone followed by 500 μL water. The mixture was stirred at room temperature for 1 h, then partitioned between EtOAc and water, adding 1 N NaOH until the aqueous phase was neutral. The organic layer was then dried over MgSO$_4$ and concentrated to give 4-{N,N-[2-(methylsulfonyl)ethyl](pyridin-2-ylmethyl)amino}phenyl methyl sulfone in 57% yield (446 mg), pure by $^1$H NMR.

Example 6

Synthesis of 4-{N,N-[2-(methylsulfonyl)ethyl](4-bromobenzyl)amino}phenyl methyl sulfone (1-12)

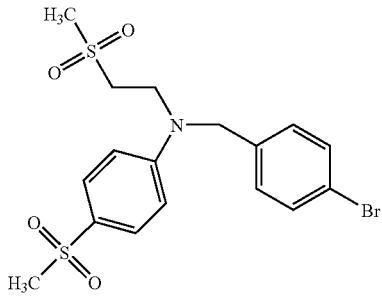

Step 1

To 8.94 ml (1.83 mmol) of 4-(methylthio)aniline dissolved in 100 ml DMF was added 1.72 g (71.67 mmol) NaH at 0° C., followed with 6.29 ml (71.80 mmol) methyl vinyl sulfone. The mixture was stirred at room temperature for 14 h, quenched with MeOH and concentrated.

The residue was dissolved in CH$_2$Cl$_2$, washed with aqueous HCl (1M) (100 ml×2), then water, dried over MgSO$_4$ and concentrated. The crude product was purified by flash chromatography (Hexane:ethyl acetate 1:1) to provide 4-[2-methylsulfonyl)ethylamino]phenyl methylthiol (3.60 g) as a yellow solid.

Step 2

A solution of 4-[2-methylsulfonyl)ethylamino]phenyl methylthiol (3.60 g; 14.67 mmol) in 200 ml MeOH and 50 ml THF was cooled to 0° C., to which a mixture of 13.57 g (22.07 mmol) OXONE™ with 50 ml warm water was added. The mixture was stirred at room temperature for 30 minute. The OXONE™ solid was filtered off and the filtrate was concentrated. A brown solid precipitated out during the concentrated, which was filtered out to provide 4-[2-methylsulfonyl)ethylamino]phenyl methyl sulfone (2.38 g).

Step 3

To a solution of 4-[2-methylsulfonyl)ethylamino]phenyl methyl sulfone (0.80 g; 2.88 mmol) in 20 ml DMF was added 0.104 g (4.33 mmol) NaH followed by 1.25 ml (9.21 mmol) 4-bromobenzyl bromide. The mixture was stirred at room temperature for 1 h, quenched with MeOH and concentrated. The residue was purified by prep-TLC (hexane:ethyl acetate 1:2) to provide 0.765 g product 4-{N,N-[2-(methylsulfonyl)ethyl](4-bromobenzyl)amino}phenyl methyl sulfone as a white foam.

Example 7

Synthesis of 4-{N,N-[2-(methylsulfonyl)ethyl](4-ethoxybenzyl)amino}phenyl methyl sulfone (1-65)

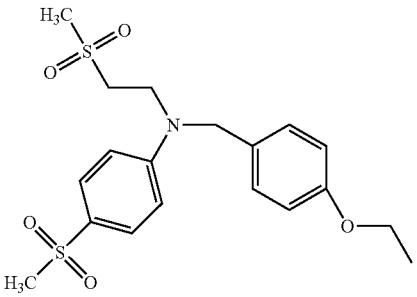

Step 1

To 8.94 ml (1.83 mmol) of 4-(methylthio)aniline dissolved in 100 ml DMF was added 1.72 g (71.67 mmol) NaH at 0° C., followed with 6.29 ml (71.80 mmol) methyl vinyl sulfone. The mixture was stirred at room temperature for 14 h, quenched with MeOH and concentrated. The residue was dissolved in CH$_2$Cl$_2$, washed with aqueous HCl (1M) (100 ml×2), then water, dried over MgSO$_4$ and concentrated. The crude product was purified by flash chromatography (Hexane:ethyl acetate 1:1) to provide 4-[2-methylsulfonyl)ethylamino]phenyl methylthiol (3.60 g) as a yellow solid.

Step 2

A solution of 4-[2-methylsulfonyl)ethylamino]phenyl methylthiol (3.60 g; 14.67 mmol) in 200 ml MeOH and 50 ml THF was cooled to 0° C., to which a mixture of 13.57 g (22.07 mmol) OXONE™ with 50 ml warm water was added. The mixture was stirred at room temperature for 30 minute. The OXONE™ solid was filtered off and the filtrate was concentrated. A brown solid precipitated out during the concentrated, which was filtered out to provide 4-[2-methylsulfonyl)ethylamino]phenyl methyl sulfone (2.38 g).

Step 3

To a solution of 4-[2-methylsulfonyl)ethylamino]phenyl methyl sulfone (0.548 g; 1.97 mmol) and 0.73 g (3.95 mmol) 4-ethoxybenzoyl chloride in anhydrous CH$_2$Cl$_2$ was added 0.32 ml (3.95 mmol) pyridine. The mixture was warmed to 45° C. and stirred for 14 h. The reaction mixture was concentrated and the residue was purified with prep-TLC (hexane:ethyl acetate 1:3) to provide 4-{N,N-[2-(methylsulfonyl)ethyl](4-ethoxybenzyl)amino}phenyl methyl sulfone (0.664 g) as a white foam.

The above product, 4-{N,N-[2-(methylsulfonyl)ethyl](4-ethoxybenzyl)amino}phenyl methyl sulfone (0.42 g; 0.98 mmol), was dissolved in 20 ml anhydrous toluene, to which 0.098 ml (0.98 mmol) BH$_3$.Me$_2$S (10.0–10.2 M) complex was added. The mixture was refluxed with stirring for 18 h, and quenched with aqueous NaHCO$_3$ (8 ml). The toluene layer was separated and the aqueous layer was extracted with CH$_2$Cl$_2$ (100 ml×3). The organic layers were combined, dried over MgSO$_4$ and concentrated. The residue was purified with prep-plate (hexane:ethyl acetate 1:2) to provide 4-{N,N-[2-(methylsulfonyl)ethyl](4-ethoxybenzyl)amino}phenyl methyl sulfone (0.143 g) product as a white foam.

Example 8

Synthesis of 4-[N,N-(4-methylsulfonylphenyl)(4-fluorobenzyl)amino]phenyl methyl sulfone (1-68) and 4-[N,N-(4-methylthiophenyl)(4-fluorobenzyl)amino]phenyl methyl sulfone (1-69)

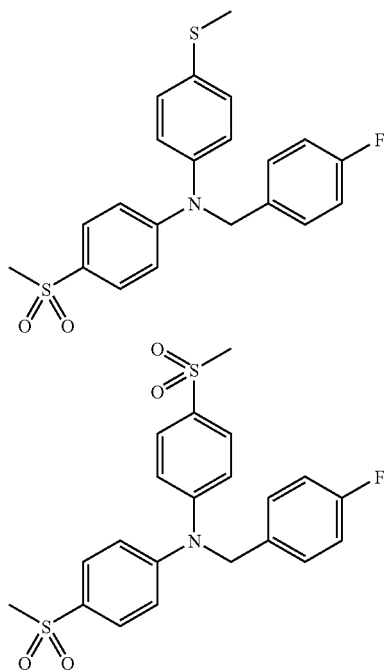

Step 1

To 150 mg (0.64 mmol) 4-bromo-phenyl methyl sulfone, 7.8 mg (2%) tris(dibenzylideneacetone)dipalladium(0), 10.6 mg (4%) BINAP, and 277 mg (0.85 mmol) $Cs_2CO_3$ in 2 mL toluene was added 63.5 μL (0.51 mmol) 4-(methylthio) aniline. The mixture was heated to 100° C. under $N_2$ and was stirred for 48 h. The mixture was cooled, diluted with ether, filtered through celite, and concentrated. Purification by column chromatography, eluting with EtOAc/hexane, provided 128 mg product 4-(4-methylsulfonyl-phenylamino) phenyl methyl sulfide, pure by $^1H$ NMR.

Step 2

To 191 mg (0.65 mmol) 4-(4-methylsulfonyl-phenylamino)phenyl methyl sulfide in 3 mL DMF was added 27 mg (0.68 mmol) sodium hydride. The mixture was stirred under $N_2$ for 15 min, then 122 μL (0.98 mmol) p-fluorobenzylbromide was added. The mixture was stirred for 18 h. The mixture was partitioned between EtOAc and water, dried over $Na_2SO_4$ and concentrated. Purification by column chromatography, eluting with EtOAc/hexane, provided 118 mg product 4-{N,N-(4-methylsulfonyl-phenyl)(4-fluorobenzyl)amino]phenyl methyl sulfide, pure by $^1H$ NMR and LCMS.

Step 3

To 138 mg (0.34 mmol) 4-{N,N-(4-methylsulfonyl-phenyl)(4-fluorobenzyl)amino]phenyl methyl sulfide and 423 mg (0.69 mmol) oxone in 3 mL methanol was added 3 drops (10% by vol) water. The mixture was stirred at room temperature for 18 h. The mixture was partitioned between EtOAc and water, dried over $Na_2SO_4$ and concentrated. Purification by column chromatography, eluting with EtOAc/hexane, provided 115 mg product 4-[N,N-(4-methylsulfonyl-phenyl)(4-fluorobenzyl)amino]phenyl methyl sulfone, pure by $^1H$ NMR and LCMS.

Example 9

Synthesis of 4-{N,N-(3-oxo-butyl)(4-fluorobenzyl)amino]phenyl methyl sulfone (1-70)

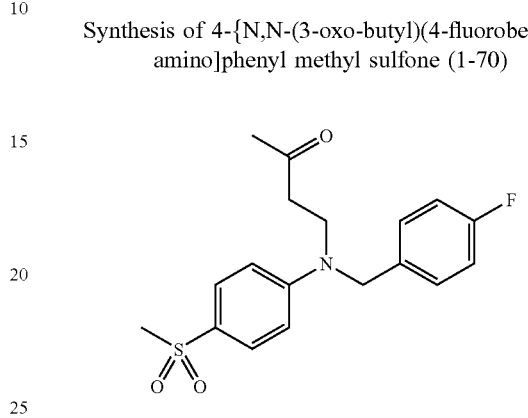

Step 1

To 2.9 mL (23 mmol) 4-methylthio-aniline and 2.9 mL (23 mmol) 4-fluorobenzylbromide in 50 mL $CH_2Cl_2$ was added 6.5 mL (47 mmol) triethylamine. The mixture was stirred at rt for 18 h. The mixture was washed with water, dried over $Na_2SO_4$ and concentrated. Purification by column chromatography, eluting with EtOAc/hexane, provided 2.2 g product 4-(4-fluorobenzylamino)phenyl methyl sulfide, pure by $^1H$ NMR.

Step 2

To 100 mg (0.40 mmol) 4-(4-fluorobenzylamino)phenyl methyl sulfide in 1 mL dioxane and 1 mL phosphate buffer [1:4 $KH_2PO_4/K_2HPO_4$ with pH 7] was added dropwise 40 μL (0.48 mmol) methyl vinyl ketone. The biphasic mixture was stirred at room temperature for 18 h. Another 40 μL (0.48 mmol) methyl vinyl ketone was added, and the mixture was stirred for 18 h. The mixture was extracted with ether, which was washed with water, dried over $Na_2SO_4$ and concentrated. Purification by column chromatography, eluting with EtOAc/hexane, did not provide separation. The crude 55 mg product 4-{N,N-(3-oxo-butyl)(4-fluorobenzyl)amino]phenyl methyl sulfide was used directly in Step 3.

Step 3

To 55 mg (0.17 mmol) 4-[N,N-(3-oxo-butyl)(4-fluorobenzyl)amino]phenyl methyl sulfide in 2 mL methanol was added 215 mg (0.35 mmol) oxone and 2 drops (10% by vol) water. The mixture was stirred at room temperature for 18 h. The mixture was partitioned between EtOAc and water, dried over $Na_2SO_4$ and concentrated. Purification by preparative TLC, developing with EtOAc/hexane, provided 5.4 mg 4-[N,N-(3-oxobutyl)(4-fluorobenzyl)amino]phenyl methyl sulfone, pure by $^1H$ NMR and LCMS.

Example 10

4-[(2-methylsulfonyl-ethyl)-(4-methyl-benzyl)-amino]-benzenesulfonamide (2-2) and 4-[(2-methylsulfonyl-ethyl)-(4-methyl-benzyl)amino]-N-(4-methoxy-benzyl)-benzenesulfonamide (2-1)

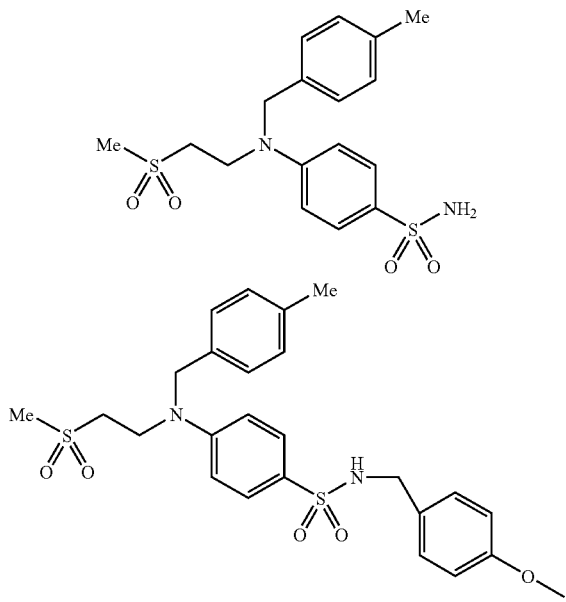

Step 1

To a 0° C. dichloromethane (300 mL) solution of 25 mL (274 mmol) of aniline was added 16 mL (123 mmol) para-toluoyl chloride over 10 min. The mixture was stirred at room temperature for 0.5 h, treated with 200 mL of ether and filtered immediately. The filtrate was washed with 1 M HCl (2×50 mL), 0.1 M NaOH (2×50 mL), and saturated aqueous ammonium chloride, dried over $Na_2SO_4$ and concentrated. Para-methylbenzanilide (17.3 g) was obtained as a tan solid and used directly.

Steps ii) and iii)

Chlorosulfonic acid (5 mL) was cooled to 0° C. under a nitrogen atmosphere and treated with para-methylbenzanilide (850 mg, 4.0 mmol). The resulting solution was stirred at room temperature for 3 h, recooled with an ice-bath, treated with ca. 25 g of ice, ca. 100 mL of saturated sodium bicarbonate and bis(para-methoxybenzyl)amine (prepared according to J. Org. Chem. 1992, 57, 7056, 1.1 g, 4.4 mmol) dissolved in ca. 50 mL of dichloromethane. The biphasic mixture was stirred vigorously at room temperature for 16 h. The layers were separated and the aqueous phase was extracted with dichloromethane, washed with brine and dried over $Na_2SO_4$. Purification by column chromatography, eluting with 1:3 ethyl acetate/hexane, provided 1.4 g of 4-[(4-methyl-benzoyl)-amino)]-[N,N-bis(4-methoxy-benzyl)]-benzenesulfonamide.

Step iv)

4-[(4-methyl-benzoyl)-amino)]-[N,N-bis(4-methoxybenzyl)]-benzenesulfonamide (1.4 g, 2.6 mmol) was dissolved in toluene (60 mL), treated with borane methyl sulfide complex (0.57 mL, 5.7 mmol) and heated to reflux for 2 h. Upon cooling, the mixture was quenched with $Na_2SO_4(H_2O)_{10}$, partitioned between pH 4 buffer and ethyl acteate, and dried over $MgSO_4$. Purification by column chromatography, eluting with 2:3 ethyl acetate/hexane, provided 1.03 g of 4-[(4-methyl-benzyl)-amino)]-[N,N-bis(4-methoxy-benzyl)]-benzenesulfonamide.

Step v)

4-[(4-methyl-benzyl)-amino]-[N,N-bis(4-methoxy-benzyl)]-benzenesulfonamide (1.03 g, 2.6 mmol) was dissolved in 6 mL of DMF at room temperature, to which methylvinyl sulfone (0.175 mL, 2.0 mmol) and sodium hydride (95%, 60 mg, 2.4 mmol) were added. The reaction was stirred at room temperature for 1.5 h, partitioned between ethyl acetate and water, dried over $MgSO_4$ and purified by column chromatography, eluting with 1:4 acetone/hexane, to provide 935 mg of 4-[(2-methylsulfonyl-ethyl)-(4-methyl-benzyl)-amino]-[N,N-bis(4-methoxy-benzyl)]-benzenesulfonamide.

Step vi)

4-[(2-methylsulfonyl-ethyl)-(4-methyl-benzyl)-amino]-[N,N-bis(4-methoxybenzyl)]-benzenesulfonamide (730 mg, 1.17 mmol) was dissoved in dichloromethane (5 mL) at room temperature and treated with trifluoroacetic acid (5 mL). After 6 h, the volatiles were removed on a rotary evaporator and the residue was partitioned between aqueous sodium bicarbonate and ethyl acetate. Following drying over $Na_2SO_4$ and removal of the volatiles, the mixture was purified by column chromatography eluting with 2:3 ethyl acetate/hexane. The first product to elute was 4-[(2-methylsulfonyl-ethyl)-(4-methyl-benzyl)amino]-N-(4-methoxy-benzyl)-benzenesulfonamide (276 mg): mp 85.7–86.6° C. The next product to elute was 4-[(2-methylsulfonyl-ethyl)-(4-methyl-benzyl)-amino]-benzenesulfonamide (184 mg): mp 169.1–170.0° C., Anal. Calcd for $C_{17}H_{22}N_2O_4S_2$ $(H_2O)_{0.6}$: C, 53.34; H, 5.77; N, 6.91. Found C, 53.33; H, 5.74; N, 7.30.

Following the procedure of Example 10, but replacing p-toluoyl chloride in Step 1 with 4-fluorobenzoyl chloride in Step 1, 4-[(2-methylsulfonyl-ethyl)-(4-fluoro-benzyl)-amino]-benzenesulfonamide was produced as an amorphous glass: Anal. Calcd for $C_{17}H_{19}FN_2O_4S_2$: C, 49.73; H, 4.96; N, 7.25. Found: C, 49.39; H, 4.96; N, 6.86. (2-3)

Following the procedure of Example 10, but replacing p-toluoyl chloride in Step 1 with 2,4-difluorobenzoyl chloride, 4-[(2-methylsulfonyl-ethyl)-(2,4-difluorobenzyl)-amino]-benzenesulfonamide was produced: mp 152.9–153.2° C. (2-4)

Example 11

3-[N,N-(2-methylsulfonyl-ethyl)(4-fluorobenzyl) amino]-pyridin-6-yl methyl sulfone (1-60)

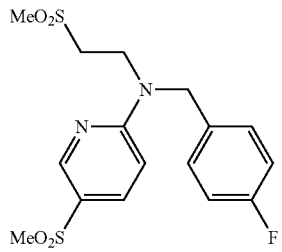

To a solution of 2.0 g (9.85 mmol) 2-bromo-5-nitropyridine dissolved in 8 mL DMF was added 690 mg (9.85 mmol) of sodium thiomethoxide. The mixture was stirred at room temperature for 1 h, and partitioned between ethyl acetate and water, dried over MgSO₄ and concentrated to obtain 1.13 g of 2-methylthio-5-nitro-pyridine, pure by ¹H NMR.

To a separatory funnel containing 646 mg (3.796 mmol) 2-methylthio-5-nitro-pyridine dissolved in 20 mL acetone and 150 mL 4 M ammonium acetate was added 26.57 mL (26.57 mmol) of a 1M solution of TiCl₃ dissolved in CH₂Cl₂/THF. The mixture was shaken for 5 min, ethyl acetate added, and partitioned, dried over MgSO₄ and concentrated. Purification by column chromatography, eluting with ethyl acetate/hexane, provided 185 mg product, 5-amino-2-methylthio-pyridine, pure by ¹H NMR.

To 344 µL (3.20 mmol) of 4-fluorobenzaldehyde and 449 mg (3.20 mmol) of 5-amino-2-methylthio-pyridine dissolved in 8 mL dichloromethane was added 1.11 g (5.25 mmol) sodium triacetoxyborohydride. The reaction mixture was stirred at room temperature for 5 h, and partitioned between ethyl acetate and water, dried over MgSO₄ and concentrated to obtain 320 mg of 5-[(4-fluorobenzyl) amino]-pyridin-2-yl methyl sulfide, pure by ¹H NMR.

To 320 mg (1.29 mmol) of 5-[(4-fluorobenzyl)amino]-pyridin-2-yl methyl sulfide dissolved in 5 mL N,N-dimethylformamide was added 137 mg (1.29 mmol) methyl vinyl sulfone followed by 30 mg (1.29 mmol) sodium hydride. The mixture was stirred at room temperature for 6 h, partitioned between EtOAc and brine, dried over MgSO₄ and concentrated. Crystallization from CH₂Cl₂/hexane afforded 447 mg of product, 5-[N,N-(2-methylsulfonyl-ethyl)(4-fluorobenzyl)amino]-pyridin-2-yl methyl sulfide, pure by ¹H NMR.

To 447 mg (1.26 mmol) of 5-[N,N-(2-methylsulfonyl-ethyl)(4-fluorobenzyl)amino]-pyridin-2-yl methyl sulfide dissolved in 5 mL methanol was added 1.55 g (2.52 mmol) oxone followed by 500 µL water. The mixture was stirred at room temperature for 2 h, then partitioned between EtOAc and water, adding 1 N NaOH until the aqueous phase was neutral. The organic layer was then dried over MgSO₄ and concentrated to obtain 387 mg product, 5-[N,N-(2-methylsulfonyl-ethyl)(4-fluorobenzyl)amino]-pyridin-2-yl methyl sulfone.

Example 12

2-[N,N-(2-methylsulfonyl-ethyl)(4-fluorobenzyl) amino]-pyridin-5-yl methyl sulfone (1-61)

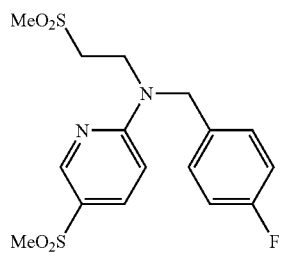

Step 1

To a solution of 16 mL of 10% H₂O₂ in 24 mL concentrated H₂SO₄ at 0° C. was added a solution of 2.34 g of 2-amino-5-bromopyridine dropwise with stirring. The ice bath was then removed, and allowed to warm to room temperature. After stirring at room temperature for 5 h, the reaction mixture was poured over ice and 1.62 g of the precipitated product, 5-bromo-2-nitro-pyridine, collected by vacuum filtration.

Step 2

To a solution of 1.0 g (4.93 mmol) 5-bromo-2-nitro-pyridine, dissolved in 10 mL DMF was added 379 mg (5.42 mmol) of sodium thiomethoxide followed by 569 mg (0.493 mmol) of tetrakis(triphenylphosphine)palladium(0). The mixture was heated to 80° C. for 2 h, cooled to room temperature, and partitioned between ethyl acetate and water, dried over MgSO₄ and concentrated. Purification by column chromatography, eluting with ethyl acetate/hexane, provided 318 mg of product, 5-methylthio-2-nitro-pyridine, pure by ¹H NMR.

Step 3

To 318 mg (1.86 mmol) of 5-methylthio-2-nitro-pyridine, dissolved in 10 mL acetone was added 7.44 mL (7.44 mmol) of a 1M solution of TiCl₃ dissolved in HCl. The mixture was stirred at room temperature for 20 min, partitioned with ethyl acetate and 1N NaOH until neutral, dried over MgSO₄ and concentrated to provide 225 mg of product, 2-amino-5-methylthio-pyridine, pure by ¹H NMR.

Step 4

To 112 µL (1.05 mmol) of 4-fluorobenzaldehyde and 147 mg (1.05 mmol) of 2-amino-5-methylthio-pyridine, dissolved in 6 mL dichloromethane was added 334 mg (1.57 mmol) sodium triacetoxyborohydride. The reaction mixture was stirred at room temperature for 4 h. The mixture was then partitioned between ethyl acetate and brine, dried over MgSO₄ and concentrated. Purification by column chromatography, eluting with ethyl acetate/hexane, provided 185 mg product, 2-[(4-fluorobenzyl)amino]-pyridin-5-yl methyl sulfide, pure by ¹H NMR.

Step 5

To 185 mg (0.744 mmol) of 2-[(4-fluorobenzyl)amino]-pyridin-5-yl methyl sulfide dissolved in 3 mL N,N-dimethylformamide was added 80 mg (0.744 mmol) methyl vinyl sulfone followed by 17 mg (0.744 mmol) sodium hydride. The mixture was stirred at room temperature for 0.25 h, partitioned between EtOAc and brine, dried over MgSO₄ and concentrated to obtain 262 mg of product, 2-[N,N-(2-methylsulfonyl-ethyl)(4-fluorobenzyl)amino]-pyridin-5-yl methyl sulfide.

Step 6

To 262 mg (0.74 mmol) of 2-[N,N-(2-methylsulfonyl-ethyl)(4-fluorobenzyl)amino]-pyridin-5-yl methyl sulfide dissolved in 3 mL methanol was added 939 mg (1.53 mmol) oxone followed by 500 µL water. The mixture was stirred at room temperature for 2 h, then partitioned between EtOAc and water, adding 1 N NaOH until the aqueous phase was neutral. The organic layer was then dried over MgSO₄ and concentrated to obtain 271 mg product of 2-[N,N-(2-methylsulfonyl-ethyl)(4-fluorobenzyl)amino]-pyridin-5-yl methyl sulfone.

Example 13

Synthesis of (4-ethoxy-benzyl)-(3-fluoro-4-methanesulfonyl-phenyl)-(2-methanesulfonyl-ethyl)-amine (1-72)

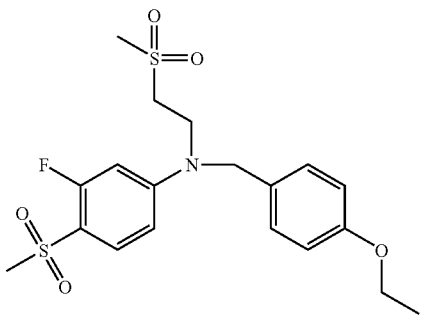

Step 1 (3-fluoro-4-thiomethyl-nitrobenzene):

A solution of 3,4-difluoronitrobenzene (5.0 g) in 65 mL dimethylformamide was treated all at once with sodium thiomethoxide (3.0 g). After stirring overnight at ambient temperature under nitrogen the mixture was diluted with water and extracted with hexanes/ethyl acetate (1/1). The organic layers were combined and washed with water and brine. Filtration of the dried organic layer through a pad of silica gel was followed by solvent removal to afford 3.98 g solid 3-fluoro-4-thiomethyl-nitrobenzene, which was carried on without characterization.

Step 2 (3-fluoro-4-thiomethyl-aniline):

A portion of the nitrobenzene from above (3.0 g) was dissolved in 40 mL of acetone and treated with titanium (III) chloride (50 mL, 1.0 M in HCl). After stirring 3 h at ambient temperature under nitrogen the reaction was cautiously quenched with NaOH (1M aqueous solution), then with sodium bicarbonate (saturated aqueous solution). Extraction with three portions of ethyl acetate was performed, then the product was washed in the aqueous phase with three portions of 5% aqueous HCl. After making the aqueous washes basic with excess aqueous NaOH (1M), the product was washed into ethyl acetate. After drying, filtration and solvent removal, 1.6 g of 3-fluoro-4-thiomethyl-aniline was recovered as an oil. This material was used without further purification or characterization.

Step 3 ((4-ethoxy-benzyl)-(3-fluoro-4-methylthio-phenyl)-amine):

The aniline from above (0.51 g, 3.24 mmol) and 4-ethoxy-benzaldehyde (0.50 g, 3.33 mmol) was dissolved in 1,2-dichloroethane (3 mL). Five drops of glacial acetic acid were added, followed by addition of sodium triacetoxyborohydride (1.2 g, 5.7 mmol). After stirring at ambient temperature over a weekend, the solution was directly poured onto a pad of silica gel and eluted with 20% ethyl acetate in hexanes. Solvent removal from the product containing fractions afforded the desired (4-ethoxy-benzyl)-(3-fluoro-4-methylthio-phenyl)-amine (1.0 g, contaminated with 4-ethoxybenzaldehyde as indicated by 1H NMR) as an oil, which was carried on to the final product as detailed below.

Step 4 ((4-ethoxy-benzyl)-(3-fluro-4-methanesulfonyl-phenyl)-(2-methanesulfonyl-ethyl)-amine:

(4-ethoxy-benzyl)-(3-fluoro-4-methylthio-phenyl)-amine from above (0.40 g) in 10 mL DMF was treated with methyl vinyl sulfone (0.35 g), followed by sodium hydride (0.12 g, 60% dispersion in mineral oil). After 3 h stirring at ambient temperature under nitrogen, the reaction was quenched with aqueous sodium bicarbonate and extracted with ethyl acetate (two extractions). The combined organic layers were washed with brine, dried over magnesium sulfate, filtered, and solvent was removed. The residue was then diluted with 17 mL of methanol and 3 mL of water were added. Oxone (1.6 g) was then added to the cooled solution (0° C.) and the reaction was allowed to warm to room temperature. After stirring overnight, the reaction was diluted with water and extracted two times with ethyl acetate. The combined organic layers dried over magnesium sulfate, filtered, and solvent was removed. Flash chromatography starting with 33% ethyl acetate in hexanes, changing to 50% ethyl acetate in hexanes and finally 66% ethyl acetate in hexanes afforded, after solvent removal, 0.29 g of the final product as a solid. mp 56–59 C. Calc. for $C_{19}H_{24}FNO_5S_2$ C, 53.13; H, 5.63; N, 3.26. Found C, 52.81; H, 5.70; N, 3.28.

Following the procedure above, but replacing 4-ethoxy-benzaldehyde with 4-fluorobenzaldehyde in Step 3 gave (4-fluoro-benzyl)-(3-fluoro-4-methanesulfonyl-phenyl)-(2-methanesulfonyl-ethyl)-amine (1-73).

Following the procedure above, but replacing 3,4-difluoro-nitrobenzene with 2-bromo-5-nitroanisole in Step 1 and 4-ethoxybenzaldehyde with 4-fluorobenzaldehyde in Step 3 gave (4-fluoro-benzyl)-(4-methanesulfonyl-3-methoxy-phenyl)-(2-methanesulfonyl-ethyl)-amine (1-74).

Example 14

4-[(2-methylsulfonyl-ethyl)-(2-methoxy-benzyl)-amino]-benzenesulfonamide (2-9)

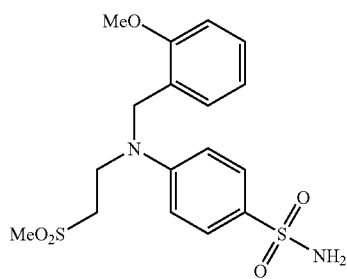

5e

Step 1

A mixture of 4-fluorophenylsulfonamide (1.4 g) and (2-thiomethyl)ethylamine (3 g) was heated at 120° C. under a nitrogen atmosphere for 4 h; the mixture was then heated at 160° C. for 2 h. The resulting dark mixture was cooled, passed through a pad of SiO₂ (hexane/EtOAc), to afford 0.34 g of 4-[(2-thiomethyl-ethyl)amino]-benzenesulfonamide as a white powder; $^1$H NMR (DMSO) δ 2.1 (s, 3H). 2.65 (m, 2H), 3.3 (m, 2H), 6.5 (t, 1H, J=5.8 Hz), 6.6 (m, 2H), 6.9 (s, 2H), 7.5 (m, 2H).

Step 2

A slurry of 4-[(2-thiomethyl-ethyl)amino]-benzenesulfonamide (0.33 g, 1.34 mmol) and 2-methoxybenzoyl chloride (0.22 mL, 0.25 g, 1.5 mmol) in (CH₂Cl)₂ was heated at reflux for 1 h. The mixture was evaporated in vacuo, and the residue was purified by MPLC (85:15 to 70:30 CH₂Cl₂/EtOAc) to afford 0.51 g (100%) of 4-[(2-methylthio-ethyl)-(2-methoxy-benzoyl)-amino]-benzenesulfonamide as a colorless glass; $^1$H NMR δ 2.09 (s, 3H), 2.70 (m, 2H), 3.62 (s, 3H), 4.1 (m, 2H), 5.25 (s, 2H), 6.67 (m, 1H), 6.86 (t, 1H, J=7.1), 7.2 (m, 4H), 7.72 (d, 2H, J=7.1).

Step 4

A solution of 1 M $BH_3$.THF/THF (6.8 mL, 6.8 mmol) was added to a solution of 4-[(2-methylthio-ethyl)-(2-methoxy-benzoyl)-amino]-benzenesulfonamide (0.51 g, 1.34 mmol) in THF (5 mL). After 18 h, the excess $BH_3$ was quenched by addition of 0.1 M HCl; followed by partitioning the mixture between $CH_2Cl_2$ and $NaHCO_3$. The organic layer was dried ($Na_2SO_4$), filtered, evaporated in vacuo, and the residue was purified by MPLC ($CH_2Cl_2$ to 70:30 $CH_2Cl_2$/EtOAc) to afford 0.38 g (77%) of 4-[(2-methylthio-ethyl)-(2-methoxy-benzyl)-amino]-benzenesulfonamide as a clear glass.

Step 5

A solution of Oxone® (1.6 g, 2.6 mmol) in $H_2O$ (5 mL) was added to a 0° C. solution of 4-[(2-methylthio-ethyl)-(2-methoxy-benzyl)-amino]-benzenesulfonamide (0.38 g, 1.0 mmol) in MeOH (21 mL) resulting in an immediate precipitate. After 1 h, the mixture was partitioned between $CH_2Cl_2$ and $H_2O$. The aqueous layer was extracted with $CH_2Cl_2$ (2×). The combined organic layer was dried ($Na_2SO_4$), filtered, evaporated in vacuo, and the residue was triturated with hot $CH_2Cl_2$ to afford, after cooling, 0.38 g (92%) of 4-[(2-methylsulfonyl-ethyl)-(2-methoxy-benzyl)-amino]-benzenesulfonamide as a white solid; $(m+H)^+$ 399.

Following the procedure of Example 14, but replacing 2-methoxybenzoyl chloride in Step 2 with 4-fluorobenzoyl chloride, 4-[(2-methylthio-ethyl)-(4-fluoro-benzoyl)-amino]-benzenesulfonamide was produced as a white solid; $^1$H NMR δ 2.16 (s, 3H), 2.77 (m, 2H), 4.14 (m, 2H), 4.8 (br s, 2H), 6.90 (dd, 2H, J=8.6, 8.6), 7.21 (d, 2H, J=8.6), 7.32 (dd, 2H, J=5.3, 8.9), 7.81 (d, 2H, J=8.5) and 4-[(2-methylthio-ethyl)-(4-fluoro-benzyl)-amino]-benzenesulfonamide (2-5), was produced as a white solid; $^1$H NMR δ 2.16 (s, 3H), 2.74 (m, 2H), 3.68 (m, 2H), 4.6 (br s, 2H), 6.1 (br s, 2H), 6.67 (d, 2H, J=9.1), 7.01 (dd, 2H, J=8.7, 8.7), 7.15 (dd, 2H, J=5.3, 8.8), 7.70 (d, 2H, J=9.1).

Following the procedure of Example 14, but replacing 2-methoxybenzoyl chloride in Step 2 with 4-ethoxybenzoyl chloride, 4-[(2-methylsulfonyl-ethyl)-(4-ethoxy-benzyl)-amino]-benzenesulfonamide, (2-6), was produced as a white solid; $(m+H)^+$ 413.

Following the procedure of Example 14, but replacing 2-methoxybenzoyl chloride in Step 2 with 2-fluorobenzoyl chloride, 4-[(2-methylsulfonyl-ethyl)-(2-fluoro-benzyl)-amino]-benzenesulfonamide, (2-7), was produced as a white solid; $(m+H)^+$ 387.

Following the procedure of Example 14, but replacing 2-methoxybenzoyl chloride in Step 2 with 2,6-difluorobenzoyl chloride, 4-[(2-methylsulfonyl-ethyl)-(2,6-difluoro-benzyl)-amino]-benzenesulfonamide, (2-8), was produced as a white solid; $(m+H)^+$ 405.

Following the procedure of Example 14, but replacing 2-methoxybenzoyl chloride in Step 2 with 2-chlorobenzoyl chloride, 4-[(2-methylsulfonyl-ethyl)-(2-chloro-benzyl)-amino]-benzenesulfonamide, (2-10), was produced as a white solid; $(m+H)^+$ 403.

Example 15

4-[(2-methylsulfonyl-ethyl)-(4-fluoro-benzyl)amino]-N-ethyl-benzenesulfonamide (2-12)

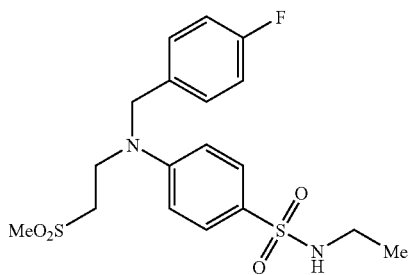

Step 1

A solution of 4-[(2-methylthio-ethyl)-(4-fluoro-benzoyl)-amino]-benzenesulfonamide (0.32 g, 0.88 mmol), acetyl chloride (0.069 mL, 76 mg, 0.97 mmol), and Et3N (0.13 mL, 97 mg, 0.96 mmol) in $CH_2Cl_2$ (9 mL) was heated at reflux for 2 h. After cooling, the mixture was evaporated in vacuo, and the residue was purified by MPLC ($CH_2Cl_2$ to 60:40 $CH_2Cl_2$/EtOAc) to afford 0.29 g (81%) of 4-[(2-methylthio-ethyl)-(4-fluoro-benzoyl)-amino]-N-acetyl-benzenesulfonamide as a colorless glass; $^1$H NMR δ 2.03 (s, 3H), 2.15 (s, 3H), 2.77 (m, 2H), 4.15 (m, 2H), 6.90 (dd, 2H, J=7.5, 7.5), 7.24 (d, 2H, J=9.0), 7.32 (dd, 2H, J=3.0, 9.0), 7.92 (d, 2H, J=9.0), 9.1 (br s, 1H).

Step 2

A solution of 1 M $BH_3$.THF/THF (7.0 mL, 7.0 mmol) was added to a stirring solution of 4-[(2-methylthio-ethyl)-(4-fluoro-benzoyl)-amino]-N-acetyl-benzenesulfonamide (0.29 g, 0.69 mmol) in THF (8 mL). After 18 h, the excess $BH_3$ was quenched by addition of 0.1 M HCl; followed by partitioning the mixture between $CH_2Cl_2$ and $NaHCO_3$. The organic layer was dried ($Na_2SO_4$), filtered, evaporated in vacuo, and the residue was purified by MPLC ($CH_2Cl_2$ to 90:10 $CH_2Cl_2$/EtOAc) to afford 0.16 g (59%) of 4-[(2-methylthio-ethyl)-(4-fluoro-benzyl)-amino]-N-ethyl-benzenesulfonamide as a colorless glass; $^1$H NMR δ 1.09 (t, 3H, J=7.5), 2.16 (s, 3H), 2.74 (m, 2H), 2.96 (m, 2H), 3.67 (m, 2H), 4.37 (t, 1H, J=6.0), 4.62 (s, 2H), 6.69 (d, 2H, J=9.0), 7.04 (dd, 2H, J=4.5, 7.5), 7.15 (dd, 2H, J=6.0, 9.0), 7.66 (d, 2H, J=7.5).

Step 3

A solution of Oxone® (0.54 g, 0.88 mmol) in $H_2O$ (2 mL) was added to a 0° C. solution of 4-[(2-methylthio-ethyl)-(4-fluoro-benzyl)-amino]-N-ethyl-benzenesulfonamide (0.13 g, 0.34 mmol) in MeOH (8 mL) resulting in an immediate precipitate. After 1 h, the mixture was partitioned between $CH_2Cl_2$ and $H_2O$. The aqueous layer was extracted with $CH_2Cl_2$ (2×). The combined organic layer was dried ($Na_2SO_4$), filtered, and evaporated in vacuo to afford 0.14 g (100%) of 4-[(2-methylsulfonyl-ethyl)-(4-fluoro-benzyl)-amino]-N-ethyl-benzenesulfonamide as a pale glass; $(m+H)^+$ 415.

Example 16

4-[(2-methylsulfonyl-ethyl)-(2-fluoro-benzyl) amino]-(N-2-fluorobenzyl)-benzenesulfonamide (2-11)

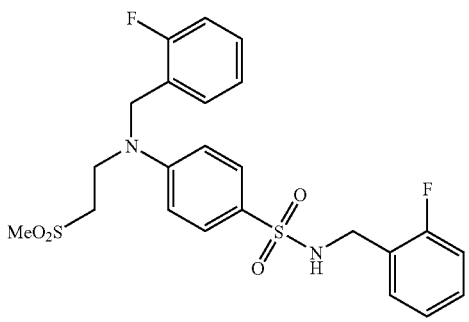

Step 1

A solution of 4-[(2-thiomethyl-ethyl)amino]-benzenesulfonamide (0.30 g, 1.2 mmol), 2-fluorobenzoyl chloride (0.29 mL, 0.39 g, 2.4 mmol), and Et3N (0.34 mL, 0.25 g, 2.4 mmol) in $CH_2Cl_2$ (12 mL) was heated at reflux for 2 h. After cooling, the mixture was evaporated in vacuo, and the residue was purified by MPLC ($CH_2Cl_2$ to 75:25 $CH_2Cl_2$/EtOAc) to afford 0.20 g (33%)of 4-[(2-methylthio-ethyl)-(2-fluoro-benzoyl)-amino]-(N-2-fluorobenzoyl)-benzenesulfonamide 3 g as a colorless glass; $^1$H NMR δ 2.13 (s, 3H), 2.74 (m, 2H), 4.13 (m, 2H), 6.80 (t, 1H, J=9.0), 7.06 (t, 1H, J=7.5), 7.17 (dd, 1H, J=7.5, 12.0), 7.2–7.3 (m, 4H), 7.36 (t, 1H, J=7.5), 7.59 (m, 1H), 7.97 (t, 1H, J=7.5), 8.02 (d, 2H, J=9.0), 9.02 (d, 1H, J=15.0).

Following the procedure of Example 15, Step 2, but replacing 4-[(2-methylthio-ethyl)-(4-fluoro-benzoyl)-amino]-N- acetyl-benzenesulfonamide with 4-[(2-methylthio-ethyl)-(2-fluoro-benzoyl)-amino]-(N-2-fluorobenzoyl)-benzenesulfonamide, was produced 4-[(2-methylsulfonyl-ethyl)-(2-fluoro-benzyl)-amino]-N-(2-fluoro-benzyl)-benzenesulfonamide as a pale glass; $(m+H)^+$ 495.

Example 17

2-Fluoro-5-{[(4-methanesulfonyl-phenyl)-(3-methanesulfonyl-propyl)-amino]-methyl}-phenol (1-79)

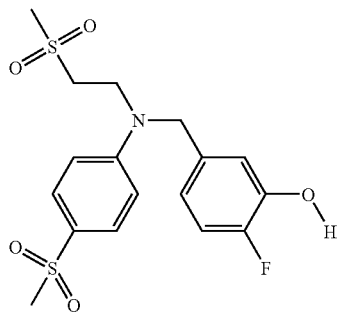

To 694 mg (1.67 mmol) of (4-fluoro-3-methoxy-benzyl)-(4-methanesulfonyl-phenyl)-(3-methanesulfonyl-propyl)-amine, prepared following the method of Example 5 but replacing 3-pyridinecarboxaldehyde with 4-fluoro-3-methoxybenxaldehyde, dissolved in 3 mL of 2,4,6-collidine was added 402 mg (3.01 mmol) lithium iodide. The mixture was heated to 150 degrees for 3 hrs, cooled to room temperature, and partitioned between ethyl acetate and 1 N HCl. Upon drying over magnesium sulfate and concentration, column chromatography, eluting with acetone/dichloromethane, provided 169 mg of 2-fluoro-5-{[(4-methanesulfonyl-phenyl)-(3-methanesulfonyl-propyl)-amino]-methyl}-phenol; $(m+H)^+$=401.

Example 18

Synthesis of (4-ethoxy-benzyl)-(4-methanesulfonyl-phenyl)-thiophen-3-ylmethyl-amine (1-76)

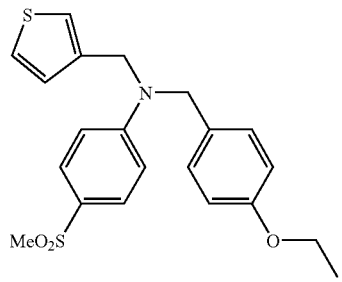

Step 1

To 5.0 mL (40.19 mmol) of 4-(methylthio)aniline dissloved in 25 mL dichloromethane was added 5.59 mL (40.19 mmol) 4-ethoxybenzaldehyde followed by 12.78 g (60.28 mmol) sodium triacetoxyborohydride. The mixture was stirred at overnight at room temperature, partitioned between EtOAc and brine, dried over $MgSO_4$ and concentrated. Crystallization from dichloromethane/hexane, provided 7.87 g of (4-Ethoxy-benzyl)-(4-methylsulfanylphenyl)-amine, pure by $^1$H NMR.

Step 2

To 200 mg (0.731 mmol) of (4-Ethoxy-benzyl)-(4-methylsulfanyl-phenyl)-amine dissolved in 5 mL dichloromethane was added 68 μL (0.731 mmol) 3-thiophenecarboxaldehyde followed by 232 mg (1.09 mmol) sodium triacetoxyborohydride. The mixture was stirred at overnight at room temperature, partitioned between EtOAc and brine, dried over $MgSO_4$ and concentrated. Column chromatography, eluting with ethyl acetate/hexane, provided 241 mg product (4-Ethoxy-benzyl)-(4-methylsulfanyl-phenyl)-thiophen-3-ylmethyl-amine, pure by $^1$H NMR.

Step 3

To 241 mg (0.652 mmol) of (4-Ethoxy-benzyl)-(4-methylsulfanyl-phenyl)-thiophen-3-ylmethyl-amine dissolved in 6 mL methanol was added 800 mg (1.3 mmol) OXONE™ followed by 600 μL water. The mixture was stirred at room temperature for 2 h, then partitioned between EtOAc and water, adding 1 N NaOH until the aqueous phase was neutral. The organic layer was then dried over $MgSO_4$ and concentrated. (4-Ethoxy-benzyl)-(4-methanesulfonyl-phenyl)-thiophen-3-ylmethyl-amine was obtained in 92% yield (240 mg) and appeared pure by $^1$H NMR.

Following the procedure of Example 18, but replacing 2-thiophenecarboxaldehyde in step 2 with 4-imidazolecarboxaldehyde gave (4-Ethoxy-benzyl)-(1H-imidazol-4-ylmethyl)-(4-methanesulfonyl-phenyl)-amine. $(m+H)^+$=385. (1-77)

Example 19

The following are representative pharmaceutical formulations containing a compound of formula (I).

Tablet formulation
The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule formulation
The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension formulation
The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable formulation
The following ingredients are mixed to form an injectable formulation.

| Ingredient | Amount |
| --- | --- |
| compound of this invention | 0.4 mg |
| sodium acetate buffer solution, 0.4M | 2.0 ml |
| HCl (1N) or NaOH (1N) | q.s. to suitable pH |
| water (distilled, sterile) | q.s. to 20 ml |

Example 20

Inhibition of COX I and COX II In Vitro

The COX I and COX II inhibitory activity of compounds of this invention in vitro was determined using partially purified COX I and COX II enzymes, prepared as described in J. Barnett et. al., *Biochim. Biophys. Acta,* 1209, 130–139 (1994).

COX I and COX II samples were diluted with Tris-HCl buffer (50 mM Tris-HCl, pH 7.9) containing 2 mM EDTA and 10% glycerol and reconstituted by incubating first with 2 mM phenol for 5 minutes and then with 1 micromolar hematin for an additional 5 minutes. 125 μl of the reconstituted COX I or COX II enzyme were preincubated for 10 minutes at room temperature in a shaking water bath with the compounds of the invention dissolved in 2–15 μl of DMSO or the carrier vehicles (control samples). The enzyme reaction was initiated by adding 25 μl of 1-[14C] arachidonic acid (80,000–100,000 cpm/tube; 20 micromolar final concentration) and the reaction was allowed to continue for an additional 45 seconds. The reaction was terminated by adding 100 μl of 2N HCl and 750 μl water. An aliquot (950 μl) of the reaction mixture was loaded onto a 1 ml $C_{18}$ Sep-Pak column (J. T. Baker, Phillipsburg, N.J.) which had been previously washed with 2–3 ml methanol and equilibrated with 5–6 ml distilled water. Oxygenated products were quantitatively eluted with 3 ml of acetonitrile/water/acetic acid (50:50:0.1, v/v) and the radioactivity in the eluate determined in a scintillation counter.

Compounds of this invention were active in this assay.

The COX inhibitory activities (expressed as $IC_{50}$, the concentration causing 50% inhibition of the COX enzyme being assayed) of some compounds of the invention were:

| CPD # | COX I $IC_{50}$, μM | COX II $IC_{50}$, μM | CPD # | COX I $IC_{50}$, μM | COX II $IC_{50}$, μM |
| --- | --- | --- | --- | --- | --- |
| 1–24 | >40 | <0.20 | 1–48 | >15 | <0.20 |
| 1–26 | >40 | <0.20 | 1–49 | >40 | <0.20 |
| 1–27 |  | <0.20 | 1–50 | >40 | <0.20 |
| 1–37 | >40 | <0.20 | 1–51 | >40 | <0.20 |
| 1–47 | >20 | <0.20 | 1–53 | >40 | <0.20 |

Example 21

Anti-inflammatory Activity

The anti-inflammatory activity of compounds of this invention may be determined by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" *Proc. Soc. Exp. Biol. Med.* 111, 544–547, (1962). This assay has been used as a primary in vivo screen for anti-inflammatory activity of most NSAIDs, and is considered predictive of human efficacy. Briefly, test materials are administered orally to female rats in a volume of 1 ml prepared as solutions or suspensions in an aqueous vehicle containing 0.9% sodium chloride, 0.5% sodium carboxymethyl-cellulose, 0.4% polysorbate 80, 0.9% benzyl alcohol and 97.3% distilled water. Control rats receive vehicle alone. After 1 h 0.05 ml of a 0.5% solution of Carrageenan (Type IV Lambda, Sigma Chemical Co.) in 0.9% saline is injected into the subplantar region of the right hind paw. Three hours later the rats are euthanized in a carbon dioxide atmosphere; hind paws are removed by severing at the tatso-crural joint; and the left and right paws are weighed. The increase in weight of the right paw over the left paw is obtained for each animal and the mean increases are calculated for each group. The anti-inflammatory activity of the test materials is expressed as the percent inhibition of the increase in hind paw weight of the test group relative to the vehicle dosed control group.

Compounds of the invention are active in this assay.

Example 22

Inhibition of Eicosanoid Synthesis In Vivo

The activity of compounds of this invention in inhibiting in vivo eicosanoid (prostaglandin $E_2$) synthesis in inflamed tissues may be determined by the carrageenan-induced inflammation (air-pouch model) in rats, using a modification of the method described in Futaki, M., et al., "Selective Inhibition of NS-398 on prostanoid production in inflamed tissue in rat Carrageenan Air-pouch Inflammation" *J. Pharm. Pharmacol.* 45, 753–755, (1993) and Masferrer, J. L., et al.; "Selective Inhibition of inducible cyclooxygenase 2 in vivo is Antiflammatory and Nonulcerogenic" *Proc. Natl. Acad. Sci. USA.* 91, 3228–3232, (1994). In this assay, an air-pouch is created in the rat and the $PGE_2$ levels in the air-pouch exudate are measured by enzyme immunoassay. Briefly, male rats are anesthetized using a 60:40 $CO_2:O_2$ mixture and subsequently injected subcutaneously with 20 ml of sterilized air, under aseptic conditions, in the proximal area of the dorsum. This injection of sterile air causes the creation of a subcutaneous "air pouch". The next day, a further 10 ml of sterile air is injected into the previously formed pouch using the same technique. The test materials are administered orally in a volume of 1 ml/100 g body weight as solutions or suspensions in an aqueous vehicle containing 0.9% sodium chloride, 0.5% sodium carboxymethyl-cellulose, 0.4% polysorbate 80, 0.9% benzyl alcohol and 97.3% water. Control rats receive vehicle alone. After 30 minutes, 5 ml of a 0.5% solution of carrageenan (Sigma, Lambda Type IV) is injected into the air pouch. The rats are euthanized 3 or 6 h after the compound administration. 10 ml of a solution containing 10 µg/l of indomethacin and 5.4 mM EDTA in 0.9% sterile saline is injected into the air pouch; the air pouch is cut open; and the exudate is harvested. The total exudate volume is recorded, and the samples are analyzed for $PGE_2$ and 6-keto $PGF_1$ by ELISA (Titerzyme®, PerSeptive Diagnostics, Boston, Mass.) and $TxB_2$ by radioimmuno assay (New England Nuclear Research, Boston Mass., Catalog No. NEK-037), according to the manufacturer's directions.

The mean concentrations of $PGE_2$ are calculated for each group. The anti-inflammatory activity of test materials is expressed as the percent inhibition of $PGE_2$ formation in the test group relative to the control group.

Example 23

Analgesic Activity

The analgesic activity of the compounds of this invention may be determined by using a modification of the method described in Randall, L. O., and Selitto, J. J., "A Method for Measurement of Analgesic Activity on Inflamed Tissue", *Arch. Int. Pharmacodyn.*, CXI, 4, 409, (1957) and Gans, et. al., "Anti-Inflammatory and Safety Profile of DuP 697, a Novel Orally Effective Prostaglandin Synthesis Inhibitor", *J. Pharmcol. Exp. Ther.,* 254, No. 1, 180, (1990). In this assay, the male Sprague Dawley rats are injected with 0.1 ml of 20% brewer's yeast in deionized water (Sigma, St. Louis) in the subplantar region of the left hind foot. After 2 h, the test materials are administered orally in a volume of 1 ml/100 g body weight as solutions or suspensions in an aqueous vehicle containing 0.9% sodium chloride, 0.5% sodium carboxymethyl-cellulose, 0.4% polysorbate 80, 0.9% benzyl alcohol and 97.3% water. Control rats receive vehicle alone. After 1 h, the hindpaw is placed on the platform of a Basile Analgesy-Meter (Ugo Biological Research Apparatus, Italy, Model #7200) and mechanical force is applied to the dorsum of the rat's hindpaw. The analgesic activity of compounds of this invention may also be determined by using an adjuvant-induced arthritis pain model in the rat, where pain is assessed by the animal's vocal response to the squeezing or flexing of an inflamed ankle joint, as described in Winter C. A. and Nuss, G. W., "Treatment of Adjuvant Arthritis in rats with Antiinflammatory Drugs", *Arthritis Rheum.,* 9, 394–403, (1966) and Winter, C. A., Kling P. J., Tocco, D. J., and Tanabe, K., "Analgesic activity of Diflunisal [MK-647; 5-(2,4-Difluorophenyl)salicylic acid] in Rats with Hyperalgesia Induced by Freund's Adjuvant", *J. Pharmacol. Exp. Ther.,* 211, 678–685, (1979).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of the formula (I):

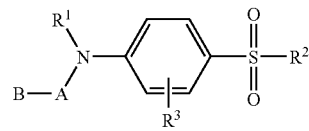

wherein
A is —$(CR_2)_n$— where n is 1, 2 or 3 and each R is independently hydrogen or alkyl;
B is substituted aryl or heteroaryl which is optionally substituted with one to four substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, unsubstituted phenyl or unsubstituted phenylalkyl) —$(CR'R'')_n$—COOR (where n is an integer from 0 to 5, R' and R'' are independently hydrogen or alkyl, and R is hydrogen, alkyl, cycloalkyl, cycloalkyl-alkyl, phenyl or phenylalkyl), or —$(CR'R'')_n$—$CONR^aR^b$ (where n is an integer from 0 to 5, R' and R'' are independently hydrogen or alkyl, and $R^a$ and $R^b$ are, independently of each other, hydrogen, alkyl, cycloalkyl, cycloalkyl-alkyl, phenyl or phenylalkyl), wherein heteroaryl is furyl, imidazolyl, pyridyl, thienyl, thiazolyl, benzothiazolyl or pyridazinyl;
$R^1$ is alkyl, alkenyl, cyanoalkyl, cycloalkyl, cycloalkylalkyl, aryl, aralalkyl, heteroaralkyl, heterocyclyl, heterocyclylalkyl, heteroalkyl or alkylcarbonylalkyl;
$R^2$ is alkyl, alkenyl, haloalkyl, cycloalkyl, cycloalkylalkyl, aryl, aralkyl, hydroxyalkyl, alkoxyalkyl, alkoxycarbonylalkyl, or $NR^{13}R^{14}$ wherein:
$R^{13}$ is hydrogen or alkyl;
$R^{14}$ is hydrogen, alkyl, alkenyl, acyl, haloalkyl, cycloalkyl, cycloalkylalkyl, aralkyl, hydroxyalkyl, alkoxyalkyl, carboxyalkyl, alkoxycarbonylalkyl, or aminoalkyl;
$R^3$ is hydrogen, alkyl, halo, nitro, cyano, hydroxy, alkoxy;

an ester, a carbamate, or a pharmaceutically acceptable salt thereof.

2. The compound of claim 1, wherein $R^3$ is hydrogen.

3. The compound of claim 2 wherein B is substituted aryl.

4. The compound of claim 3 wherein B is substituted phenyl.

5. The compound of claim 4 wherein $R^1$ is alkyl, cycloalkyl, cycloalkyl-alkyl, heterocyclyl, heterocyclylalkyl or heteroalkyl.

6. The compound of claim 5 wherein $R^1$ is heteroalkyl.

7. The compound of claim 6 wherein $R^1$ is alkylsulfonylalkyl.

8. The compound of claim 7 wherein $R^2$ is alkyl.

9. The compound of claim 8 wherein A is —(CH$^2$)—.

10. The compound of claim 7 wherein $R^2$ is $NR^{13}R^{14}$ wherein $R^{13}$ and $R^{14}$ are hydrogen.

11. The compound of claim 10 wherein A is —(CH$_2$)—.

12. The compound of claim 2 wherein B is optionally substituted heteroaryl, wherein heteroaryl is furyl, imidazolyl, pyridyl, thienyl, thiazolyl, benzothiazolyl or pyridazinyl.

13. The compound of claim 12 wherein $R^1$ is alkyl, cycloalkyl, cycloalkyl-alkyl, heterocyclyl, heterocyclylalkyl or heteroalkyl.

14. The compound of claim 13 wherein $R^1$ is heteroalkyl.

15. The compound of claim 14 wherein $R^1$ alkylsulfonylalkyl.

16. The compound of claim 15 wherein $R^2$ is alkyl.

17. The compound of claim 16 wherein A is —(CH$_2$)—.

18. The compound of claim 15 wherein $R^2$ is $NR^{13}R^{14}$ wherein $R^{13}$ and $R^{14}$ are hydrogen.

19. The compound of claim 18 wherein A is —(CH$^2$)—.

20. The compound of claim 1 wherein:
$R^1$ is heteroalkyl, wherein heteroalkyl is alkylsulfonylalkyl; and
B is substituted aryl.

21. The compound of claim 20, wherein $R^2$ is alkyl.

22. The compound of claim 21, wherein A is —(CH$_2$)—.

23. The compound of claim 20, wherein $R^2$ is $NH_2$.

24. The compound of claim 23, wherein A is —(CH$_2$)—.

25. A pharmaceutical composition comprising a therapeutically effective amount of a compound of claim 1 and a pharmaceutically acceptable excipient.

* * * * *